(12) United States Patent
Gale et al.

(10) Patent No.: US 8,263,392 B2
(45) Date of Patent: Sep. 11, 2012

(54) METHODS AND COMPOSITIONS RELATED TO CONTINUOUS FLOW THERMAL GRADIENT PCR

(75) Inventors: Bruce Kent Gale, Taylorsville, UT (US); Niel Davenport Crews, Ruston, LA (US); Carl Thomas Wittwer, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 127 days.

(21) Appl. No.: 12/514,671

(22) PCT Filed: Nov. 14, 2007

(86) PCT No.: PCT/US2007/084652
§ 371 (c)(1),
(2), (4) Date: Jul. 6, 2009

(87) PCT Pub. No.: WO2008/061129
PCT Pub. Date: May 22, 2008

(65) Prior Publication Data
US 2010/0167288 A1    Jul. 1, 2010

Related U.S. Application Data

(60) Provisional application No. 60/859,161, filed on Nov. 14, 2006.

(51) Int. Cl.
*C12M 1/34* (2006.01)
*C12Q 1/68* (2006.01)
*C12P 19/34* (2006.01)

(52) U.S. Cl. .................... 435/288.5; 435/6.12; 435/91.2

(58) Field of Classification Search .................... None
See application file for complete search history.

(56) References Cited

U.S. PATENT DOCUMENTS

| | | | | |
|---|---|---|---|---|
| 2001/0046701 | A1 | 11/2001 | Schulte | 435/287.2 |
| 2003/0104466 | A1 | 6/2003 | Knapp | 435/6 |
| 2004/0096958 | A1 | 5/2004 | Pottathil | 435/287.2 |
| 2004/0197810 | A1 | 10/2004 | Takenaka | 435/6 |

OTHER PUBLICATIONS

Bartholomeusz et al. Xurography: rapid prototyping of microstructures using a cutting plotter. J. Microelectromech. Sys. (2005) vol. 14, No. 6, pp. 1364-1374.*
Belgrader, P. et al. "A reusable flow-through polymerase chain reaction instrument for the continuous monitoring of infectious biological agents." *Analytical Chemistry*, 75: 3446-3450 (2003).
Cao, W. et al. "Chitosan as a polymer for pH-induced DNA Capture in a totally aqueous system." *Analytical Chemistry*, 78:7222-7228 (2006).
Chiou, J. et al. "A closed-cycle capillary polymerase chain reaction machine." *Analytical Chemistry* 73:2018-2021 (2001).
Easley, C. et al. "A fully integrated microfludic genetic analysis system with sample-in-answer-out capability." *PNAS* 103:19272-19277 (2006).
Fukuba, T. et al. "Microfabricated flow-through device for DNA amplification-towards in situ gene analysis." *Chemical Engineering Journal* 101:151-156 (2004).
Garstecki, P. et al. "Formation of droplets and bubbles in a microfluidic T-junction-scaling and mechanism of break-up." *Lab on a Chip*, 6:437-446 (2006).
Handyside, A. et al. "Pregnancies from biopsied human preimplantation embryos sexed by Y-specific DNA amplification." *Nature*, 344:768-770 (1990).
Hashimoto, M. e al. "Rapid PCR in a continuous flow device." *Lab on a Chip*, 4:638-645 (2004).
Herrmann, M. et al. "Amplicon DNA melting analysis for mutation scanning and genotyping: cross-platform comparison of instruments and dyes." *Clinical Chemistry* 52:494-503 (2006).
Higuchi, R. et al. "Kinetic PCR analysis: real-time monitoring of DNA amplification reactions." *Bio/Technology* 11:1026-1030 (1993).
Hill, C. et al. "Detection and identification of cytochrome P-450 2C9 alleles *1, *2 and *3 by high-resolution melting curve analysis of PCR amplicons." *Am J Clin Pathol*, 125:584-591 (2006).
Jendrejack, R. et al. "DNA dynamics in a microchannel." *J. Physical Review Letters* 91(3):038102-1-038102-4 (2003).
Kopp, M et al. "Chemical amplification: continuous-flow PCR on a chip." *Science* 280:1046-1048 (1998).
Lapham, J.et al. "Measurement of diffusion constants for nucleic acids by NMR." *Journal of Biomolecular NMR* 10:255-262 (1997).
Li, S. et al. "A continuous-flow polymerase chain reaction microchip with regional velocity control." *Journal of Microelectromechanical Systems*, 15(1):223-236 (2006).
Mao, H. et al. "Reusable platforms for high-throughput on-chip temperature gradient assays." *Analytical Chemistry*, 74:5071-5075 (2002).
Morrison, T. et al. "Nanoliter high throughput quantitative PCR." *Nucl. Acids Res.* 34 (18):e123 (1-9) (2006).
Nakayama, T. et al. "Circumventing air bubbles in microfluidic systems and quantitative continuous-flow PCR applications." *Analytical and Bioanalytical Chemistry*, 386:1327-1333 (2006).
Neuzil, P. et al. "Disposable red-time microPCR device: lab-on-a-chip at a low cost." *Molecular Biosystems*, 2:292-298 (2006).
Northrup, M. et al. "A miniature analytical instrument for nucleic acids based on micromachined silicon reaction chambers." *Anal. Chem.* 70(5):918-922 (1998).
Obeid, P. and Christopoulos, T. "Continuous-flow DNA and RNA amplification chip combined with laser-induced fluorescence detection." *Analytica Chimica Acta* 494:1-9 (2003).
Obeid, P. et al. "Microfabricated device for DNA and RNA amplification by continuous-flow polymerase chain reaction and reverse transcription-polymerase chain reaction with cycle number selection." *Analytical Chemistry* 75:288-295 (2003).
Pappaert, K. et al. "Measurements of diffusion coefficients in 1-D micro- and nanochannels using shear-driven flows." *Lab on a Chip* 5:1104-1110 (2005).
Ririe, K. et al. "Product differentiation by analysis of DNA melting curves during the polymerase chain reaction." *Analytical Biochemistry*, 245:154-160 (1997).
Roper, M. et al. "Infrared temperature control system for a completely noncontact polymerase chain reaction in microfluidic chips." *Analytical Chemistry* 79:1294-1300 (2007).

(Continued)

*Primary Examiner* — Kenneth R. Horlick
*Assistant Examiner* — David Thomas
(74) *Attorney, Agent, or Firm* — Ballard Spahr LLP

(57) ABSTRACT

Disclosed are compositions and a method for amplification and detection of nucleic acid sequences based on continuous flow thermal gradient PCR.

53 Claims, 16 Drawing Sheets

OTHER PUBLICATIONS

Schneegass, I. et al. "Miniaturized flow-through PCR with different template types in a silicon chip thermocycler." *Lab on a Chip*, 1:42-49 (2001).

Simpson, P. "Microfabrication technology for the production of capillary array electrophoresis chips." *Biomedical Microdevices* 1:7-25 (1998).

Sun, K. et al. "A heater-integrated transparent microchannel chip for continuous-flow PCR." *Sensors and Actuators B* 84:283-289 (2002).

Sundberg, S. et al. "Solution-phase DNA mutation scanning and SNP genotyping by nanoliter melting analysis." *Biomedical Microdevices*, 9:159-166 (2007).

Wang, H. et al. "Continuous flow thermal cycler microchip for DNA cycle sequencing." *Analytical Chemistry* 78(17):6223-6231 (2006).

Wittwer, C. et al. "Rapid cycle DNA amplification." *The Polymerase Chain Reaction*; Mullis, K. B., Ferre, F., Gibbs, R., Eds.; Springer-Verlag: Deerfield Beach, pp. 174-181 (1994).

Wittwer, C. et al. "High-resolution genotyping by amplicon melting analysis using LCGreen." *Clin Chem*, 49(6):853-860 (2003).

Wittwer, C. and Hermann, M. "Rapid thermal cycling and PCR kinetics." In PCR Applications: Protocols for Functional Genomics, 1 ed.; Innis, M. A., Gelfand, D. H., Sninsky, J. J., Eds.; Academic Press: San Diego, pp. 211-229 (1999).

Yang, M. et al. "Cost-effective thermal isolation techniques for use on microfabricated DNA amplification and analysis devices." *J. Micromech. Microeng.* 15:221-230 (2005).

Zhang, C. et al. "PCR microfluidic devices for DNA amplification." *Biotechnology Advances*, 24:243-284 (2006).

Zhang, C. and Xing, D. "Survey and Summary: Miniaturized PCR chips for nucleic acid amplification and analysis: latest advances and future trends." *Nucl. Acids Res.*, 35(13):4223-4237 (2007).

Zhou, L. et al. "High-resolution DNA melting analysis for simultaneous mutation scanning and genotyping in solution." *Clinical Chemistry*, 51:1770-1777 (2005).

* cited by examiner

FIGURE 4A & B
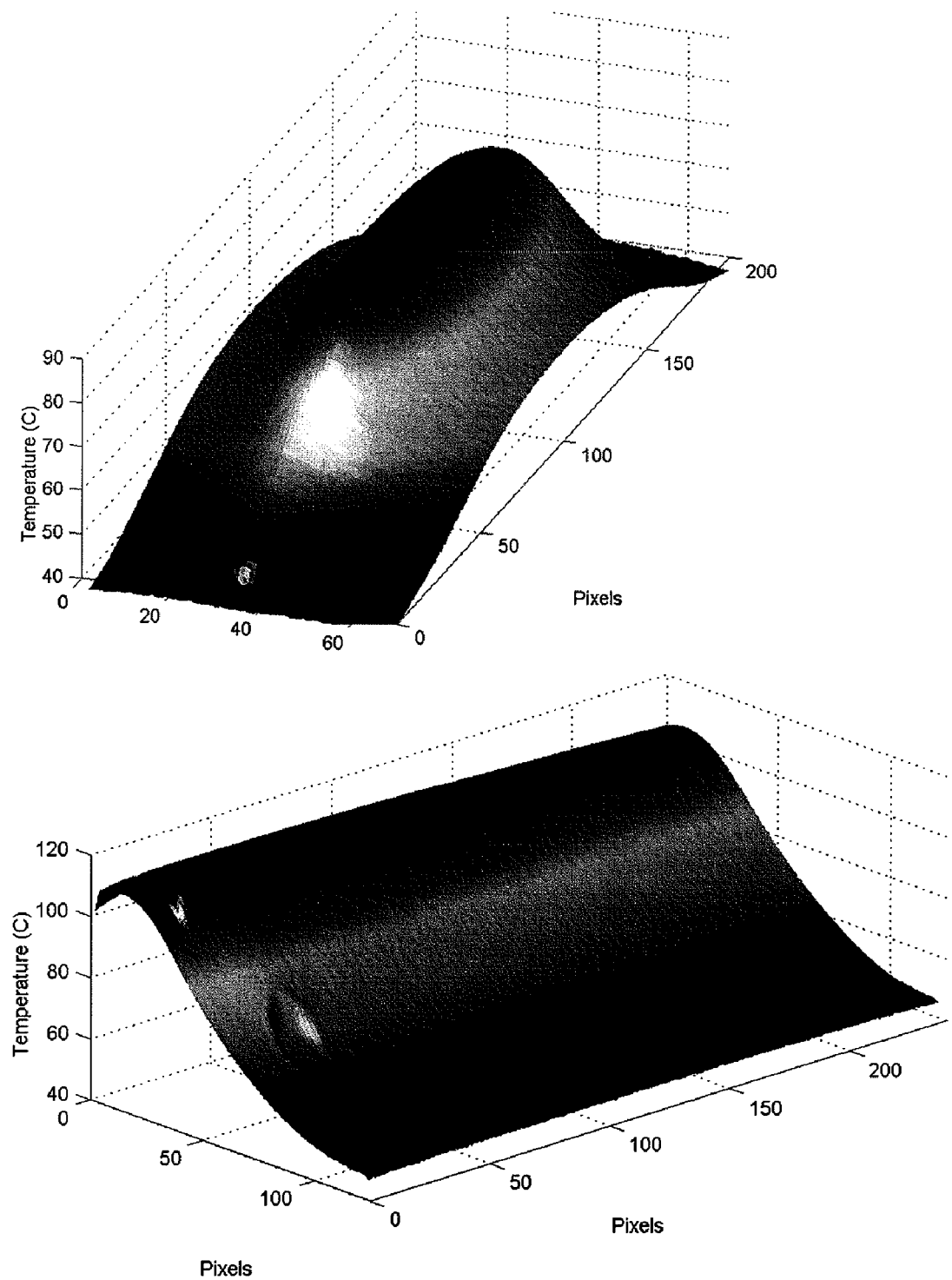

METHODS AND COMPOSITIONS RELATED TO CONTINUOUS FLOW THERMAL GRADIENT PCR

CROSS-REFERENCE TO RELATED APPLICATION

This application claims priority to provisional U.S. Patent Application Ser. No. 60/859,161, filed on Nov. 14, 2006, in the United States Patent and Trademark Office, the provisions of which are incorporated fully herein by this reference.

STATEMENT REGARDING FEDERALLY FUNDED RESEARCH

This invention was made with government support under Grant #DGE-9987616 awarded by the National Science Foundation. The government has certain rights in this invention.

BACKGROUND OF THE INVENTION

The disclosed invention is in the general field of nucleic acid amplification and detection, and specifically in the field of amplification through continuous flow mechanisms.

Continuous-flow polymerase chain reaction (CF-PCR) is an amplification technique in which a single fluidic channel is heated with spatial temperature variations such that a flowing sample experiences the thermal cycling required to induce amplification. This heating method reduces the thermal load to only that of the sample being amplified. By excluding the substrate from the thermal cycling, lower energy consumption and faster cycling can be achieved. This has been demonstrated with a variety of thermocycling techniques, including infrared (IR) heated PCR systems (Roper, 2007), shuttle PCR devices (Chiou, 2001), and CF-PCR instrumentation. CF-PCR was first demonstrated in a microfluidic device Kopp and coworkers (Kopp, 1998). This foundational design consisted of a microfluidic serpentine channel embedded within a glass substrate. Three heaters were fixed to the chip to produce distinct thermal zones through which the fluid would pass. Other researchers have continued to improve the operation of this original 20-cycle device. Li and coworkers (Li, 2006) built a device whose 20-cycle serpentine microchannel was narrower in the regions between the three temperature zones, thus reducing the inter-temperature transition time. Schneegass and coworkers (Schneegass, 2001) built a 25-cycle device from silicon and glass. The device included integrated heaters and temperature sensors which were fabricated on-chip using IC manufacturing technology. Fukuba and coworkers (Fukuba, 2004) were able to automate the operation of a 30-cycle device using miniature pumps and valves. Sun and coworkers (Sun, 2002) have developed a 30-cycle CF-PCR device with integrated ITO heaters (indium tin oxide), thus making the device optically transparent. Obeid and coworkers (Obeid, 2003b) presented a device capable of the reverse transcription of RNA prior to its amplification in a 40-cycle serpentine channel (RT-PCR). The device was fabricated with outlets at cycle numbers 20, 25, 30, 35, and the full 40. In addition, the researchers were able demonstrate amplification with plug flow, thus reducing the amplification volume to only 2 μl per amplified sample. While these previous projects do represent significant improvements for CF-PCR, they all implement the original heating scheme: multiple zones of distinct temperatures, placed in parallel, through which a serpentine channel repeatedly passes. An alternative layout was presented by Hashimoto and coworkers (Hashimoto, 2004), who developed a device in which the isothermal zones were separated into the four quadrants of a rectangular substrate. By fabricating a 20-loop spiral microchannel which passes repeatedly through each zone, the flowing fluid was able to experience the required thermocycling.

Integration of these continuous-flow amplification systems is currently being accomplished by several groups. Obeid and coworkers (Obeid, 2003a) have combined a continuous-flow RT-PCR with an laser-induced fluorescence (LIF) detection system. Nakayama and coworkers (Nakayama, 2006) have demonstrated real-time amplification detection using TaqMan technology. Wang and coworkers (Wang, 2006) have used a quadrant heating/spiral channel CF-PCR device as an amplification module within a Sanger sequencing system. In addition, other technologies are being developed that could potentially be included to form a complete "Lab-on-a-chip", such as continuous-flow DNA extraction (Cao, 2006) and sample mixing (Garstecki, 2006).

The further miniaturization and simplification of the CF-PCR device is critical for this technology to compete against other micro-PCR methods. Researchers have shown that by including insulating features in the fabricated devices, better thermal separation between the several temperature zones is possible (Hashimoto, 2004; Schneegass, 2001; Yang, 2005). While this allows for a reduction in the spacing between the heaters, thermal "cross-talk" ultimately limits the proximity of the isothermal regions (Li, 2006). Thus, the need for multiple isolated temperature zones greatly complicates further reduction in the CF-PCR footprint.

BRIEF SUMMARY OF THE INVENTION

Disclosed herein is a device for replicating nucleic acid, said device comprising: a microchannel extending from an inlet port to an outlet port; and a heater for producing a spatial temperature gradient.

Also disclosed is a device for replicating a nucleic acid, said device comprising: a microchannel; two plates; and a heater; wherein the microchannel is sandwiched between the two plates and the heater is operable to form a spatial temperature gradient across the microchannel.

Further disclosed is a device for replicating nucleic acid, said device comprising: a channel having a plurality of sections forming a continuous pattern; and a heater disposed along a centerline of the continuous pattern; wherein each section of the channel comprises a first portion and a second portion, the first portion of the channel being narrower than the second portion of the channel.

Disclosed herein is a method of amplifying a nucleic acid, the method comprising the steps of: a) forming a steady state temperature gradient on a device comprising microchannels; and b) exposing a nucleic acid to the temperature gradient in a manner conducive for amplification; thereby amplifying a nucleic acid.

Also disclosed is a method for monitoring nucleic acid replication using a microchip, said method comprising the steps of: a) forming a temperature gradient across a device; and b) exposing a nucleic acid to the temperature gradient in a manner conducive for amplification; and c) detecting nucleic acid amplification using fluorescent monitoring; thereby monitoring nucleic acid amplification using a microchip.

Further disclosed is a method of forming a chip with microchannels for use in continuous-flow PCR, said method comprising the steps of: a) creating a digital image of the microchannels using a digital computing machine; b) sending the digital image of the microchannels to a plotting device such that the plotting device forms the microchannels on a thin film; and c) sandwiching the thin film between two plates; thereby forming a chip with microchannels for use in continuous-flow PCR.

BRIEF DESCRIPTION OF THE DRAWINGS

FIG. 1A shows a centerline heating assembly, while FIG. 1B shows an edge heating assembly. Aluminum pieces thermally interface the glass chip with the heaters and cooling fins, ensuring a uniform temperature gradient across the glass. The Teflon pieces hold the heating elements in place.

FIG. 1 shows the mask geometry for the 30-cycle PCR chip shows the layout of the serpentine channel. The channel is etched into 25 mm×75 mm glass pieces. The mask dimensions for the wide and narrow regions are 550 µm and 10 µm, respectively. Considering the isotropic nature of the etchant, the final widths of the channel are 650 µm and 110 µm, respectively. Microfluidic channel geometries associated with A) the centerline heating device, and B) the edge heating apparatus. The masks shown correspond to A) the rapid prototyping technique, and B) the photolithographic etching technique.

FIG. 4 shows the temperature gradient of the glass surface above the microfluidic channel is nearly linear at 3.5° C./mm (+/−1° C./mm). Since the activity of the DNA polymerase enzyme limits the allowable ramp rates between the annealing and extension temperatures, the shallower gradient at lower temperatures is advantageous.

DETAILED DESCRIPTION OF THE INVENTION

DEFINITIONS

Figure 1:
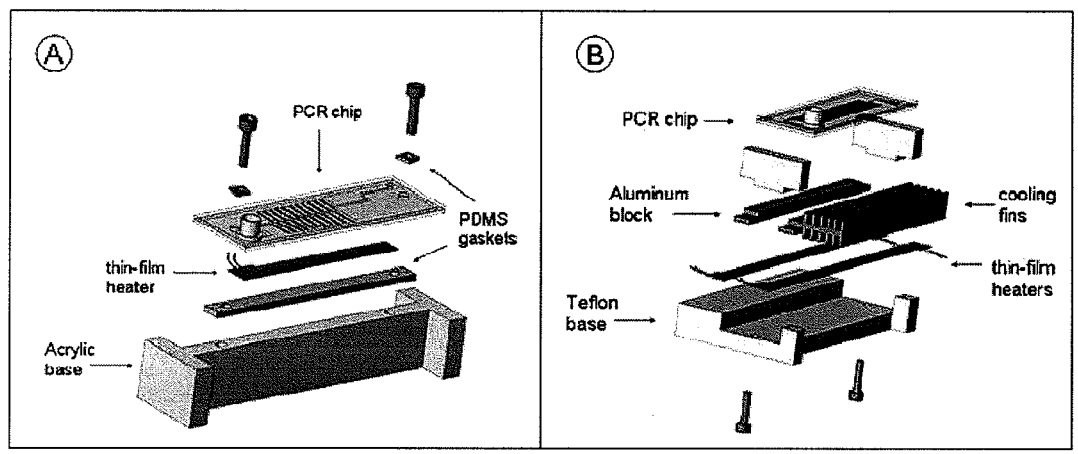
FIG. 1 shows an exploded diagram of the heating apparatus designed for use with thermal gradient PCR.

A "cyclic polymerase-mediated reaction" refers to a biochemical reaction in which a template molecule or a population of template molecules is periodically and repeatedly copied to create a complementary template molecule or complementary template molecules, thereby increasing the number of the template molecules over time. Generally, a "cyclic polymerase-mediated reaction" includes primer molecules that serve to initiate synthesis of the complementary template, a polymerase enzyme that catalyzes the synthesis, and monomeric molecules that make up the template. In each cycle of a "cyclic polymerase-mediated reaction" not every template will necessarily by copied, and each complementary template whose synthesis is initiated in a cycle will not necessarily be completed. In preferred embodiments of this invention, the template and primer molecules are nucleic acids, the monomeric units are nucleotides, and the polymerase is a DNA or RNA polymerase.

A "polymerase" is an enzyme that catalyzes the sequential addition of monomeric units to a polymeric chain, or links two or more monomeric units to initiate a polymeric chain. In preferred embodiments of this invention, the "polymerase" will work by adding monomeric units whose identity is determined by and which is complementary to a template molecule of a specific sequence. For example, DNA polymerases such as DNA pol 1 and Taq polymerase add deoxyribonucleotides to the 3' end of a polynucleotide chain in a template-dependent manner, thereby synthesizing a nucleic acid that is complementary to the template molecule.

A "template molecule" refers to a molecule of specific identity which can serve as a template for the synthesis of a complementary molecule. Most often, a "template molecule" is a polymeric molecule. In preferred embodiments, a "template molecule" is a nucleic acid, e.g. DNA, RNA, a nucleic acid comprising both deoxyribo-and ribonucleotides, or a nucleic acid comprising deoxyribonucleotides, ribonucleotides, and/or analogs and derivatives thereof. In the context of PCR, a "template molecule" may represent a fragment or fraction of the nucleic acids added to the reaction. Specifically, a "template molecule" refers to the sequence between and including the two primers.

The "duplication" of a template molecule refers to the synthesis of a molecule that is complementary to the template molecule. In the context of this invention, "duplication" generally involves an incubation in the presence of a primer molecule, polymerase, and nucleotides. For PCR, "duplication" refers to the synthesis of a nucleic acid that spans the sequence between two primers. Thus, if two primers cover a region that comprises a fragment of a nucleic acid added to a reaction, the duplication refers to the synthesis of the nucleic acid, complementary to the added nucleic acid, that spans the region between the two primers.

When reagents are said to be present in "non-rate limiting amounts," this means that the kinetics of the reaction are not primarily determined by the availability of the reagents. In the course of a PCR, when the primer molecules and the polymerase are present in "non-rate limiting amounts," then the kinetics of an extension step of the PCR will generally be determined by factors such as the enzymatic activity, rate, and processivity of the polymerase, the size of the template, etc.

"PCR" refers to a polymerase chain reaction, which is a themocyclic, polymerase-mediated, DNA amplification reaction. A PCR typically includes template molecules, oligonucleotide primers complementary to each strand of the template molecules, a thermostable DNA polymerase, and deoxyribonucleotides.

A "microfluidic device" is an apparatus or a component of an apparatus that has one or more microfluidic reaction channels and/or chambers. Typically, at least one reaction channel or chamber of a microfluidic device has a cross-sectional dimension between about 0.1 μm and about 500 μm.

A "microchannel" refers to the channel in which the PCR reaction occurs. It can have a cross sectional dimension between about 0.1 μm and about 500 μm. It can be one of many shapes, which will be appreciated by those of skill in the art. Examples include linear, serpentine, and circular, for example.

"Denaturation" of a template molecule refers to the unfolding or other alteration of the structure of a template so as to make the template accessible to duplication. In the case of DNA, "denaturation" refers to the separation of the two complementary strands of the double helix, thereby creating two complementary, single stranded template molecules. "Denaturation" can be accomplished in any of a variety of ways, including by heat or by treatment of the DNA with a base or other denaturant.

A "single stranded template molecule" refers to a denatured template molecule to which a complementary nucleic acid can bind.

"Hybridization" of two nucleic acids refers to the binding of two complementary, single stranded nucleic acids to form a double-stranded nucleic acid.

The "extension of the primer molecules" refers to the addition of nucleotides to a primer molecule so as to synthesize a nucleic acid complementary to a template molecule. "Extension of the primer molecules" does not necessarily imply that the primer molecule is extended to synthesize a complete complementary template molecule. Rather, even if only a fraction of the template molecule has been copied, the primer is still said to be extended.

A "thermocyclic reaction" is a multi-step reaction wherein at least two steps are accomplished by changing the temperature of the reaction.

A "detectable amount of product" refers to an amount of amplified nucleic acid that can be detected using standard laboratory tools. PCR products can be labeled with a detectable marker, separated electrophoretically, and detected visually or using a standard automated detection system such as the Fluor-S MultiImager System (Bio-Rad laboratories) or the Nucleovision from Nucleotech (San Mateo, Calif.). Generally, a "detectable amount of product" is between about 10 ng and about 100 ng of DNA.

When a template is said to be derived from "humans", "mammals", "vertebrates", "insects", "bacteria", "fungi", "plants", or "viruses", it means that the template comprises a nucleic acid whose sequence represents, or corresponds to, a sequence naturally found in the nuclear or mitochondrial genome of one of these types of organisms. The template may be removed directly from such an organism or from biological material originating ill such an organism, or may be obtained otherwise, such as by synthesis using standard laboratory technology to conform to a known sequence.

A "target nucleic acid" refers to a nucleic acid of specific sequence, derived from any of a number of sources, including humans, mammals, vertebrates, insects, bacteria, fungi, plants, and viruses. In certain embodiments, the target nucleic acid is a nucleic acid whose presence or absence can be used for certain medical or forensic purposes such as diagnosis, DNA fingerprinting, etc.

A "detectable marker" refers to a nucleotide analog that allows detection using visual or other means. For example, fluorescently labeled nucleotides can be incorporated into a nucleic acid during one or more steps of a cyclic polymerase-mediated reaction, thereby allowing the detection of the product of the reaction using, e.g. fluorescence microscopy or other fluorescence-detection instrumentation.

A "separation step" refers to the isolation of an amplified nucleic acid. In certain embodiments, the isolated nucleic acid is used to determine the amount of amplified product or to sequence the amplified product. A "separation step" does not necessarily entail the isolation of all of the amplified product, or that the isolation occurs following a final cycle of the reaction. Instead, a "separation step" can occur at any time during the reaction, and can indicate the isolation of only a fraction of the amplified product.

A "reduced-time cycle" or "rapid PCR" refers to a cycle of a PCR, comprising denaturation, annealing, and hybridization steps, that is of shorter duration than an analogous step under standard reaction conditions. In general, such standard conditions are set to allow the duplication of a high percentage of template molecules. Such standard steps generally last about 1 minute per 1 kilobase of template DNA. A reduced-time cycle is typically on the order of 0.1-10 seconds, and is defined as a cycle of less than 60 seconds.

A "full-time cycle" refers to a cycle of a PCR performed under standard reaction conditions, which is designed to allow the maximum duplication of the templates in the PCR. Generally, such "full-time cycles" are on the order of about 1 minute per kilobase of template DNA.

An "increased number of reduced-time cycles" refers to a number of PCR cycles that is greater than a standard number of full-time extension steps. Generally, the "increased number of reduced-time extension steps" is determined by the number of PCR cycles required to generate a detectable amount of product using a reduced-time extension step. Typically, an "increased number of reduced-time extension steps" is at least about 30, but can refer to 50 or more cycles.

A "standard number of full-time extension steps" refers to the number of cycles of a PCR that are generally carried out under standard conditions. For most applications, this number is about 20 to 30, and corresponds to the number of cycles required to generate a detectable amount of product using standard conditions, including a full-time extension step.

A "thermostable polymerase" refers to a DNA or RNA polymerase enzyme that can withstand extremely high temperatures, such as those approaching 100° C. Often, thermostable polymerases are derived from organisms that live in extreme temperatures, such as *Thermus aquaticus*. Examples of thermostable polymerases include, Taq, Tth, Pfu, Vent, deep vent, UITma, and variations and derivatives thereof.

GENERAL DESCRIPTION

A continuous-flow PCR microfluidic device has been developed in which the target DNA product can be detected and identified during its amplification, thus eliminating any requirement for further post-PCR analysis. Multiple small (<200 bp) targets have been serially amplified from human genomic DNA. With an intercalating dye in the PCR mixture, the amplification and denaturing behavior of each sample has been observed and differentiated by analyzing a single photograph (Example 2). Since the progression of the PCR in the continuous-flow thermal gradient microdevice is spread spatially throughout its serpentine geometry, a full device (~6 µl volume) contains sample simultaneously at each cycle and temperature within the PCR. The denaturing behavior of the amplifying DNA, which depends on its specific size, sequence, and composition, occurs spatially, and has been photographed. Corresponding DNA melting curves have been generated, from which the several DNA samples can be identified. This is the first reported demonstration of a melting analysis of amplified DNA from a single image acquisition. Also, given that the majority of PCR cycles can be imaged in a single photograph, this DNA analysis can be performed at any cycle that contains a significant quantity of amplicon. Thus, this system also eliminates the cycle-selection challenges typically associated with continuous-flow PCR microfluidics.

The polymerase chain reaction (PCR) involves the repetition of three consecutive bio-chemical processes: the denaturing, or melting, of double-stranded DNA (ds-DNA) into single-stranded DNA (ss-DNA), the annealing of short oligonucleotide primers to the ss-DNA, and the full extension of the primers by a DNA polymerase. Each reaction occurs within a small range of temperatures, and the reaction kinetics is determined by the specific constituents. The annealing of primers occurs in less than one second, at a temperature determined by the size and sequence of the oligonucleotides used (commonly between 55° C. and 60° C.). The extension of the polymerase can occur at a rate approaching 100 bases per second, with optimum activity at around 72° C. (Wittwer 1994). The precise melting behavior of the DNA is unique to its size, sequence, and molecular composition (primarily, the ratio of guanine-cytosine bonds to adenine-thymine bonds, or G-C %). The denaturing of DNA occurs in less than one second, at temperatures from 80° C. or lower (for small targets with a low G-C %) to 95° C. (for human genomic DNA). Since a unique amount of thermal energy is needed to denature (melt) a specific pattern of paired nucleotides, differing DNA samples can exhibit characteristic melting signatures. When this behavior is monitored with very high precision, sequence variations of only a single base pair can be distinguished (Wittwer 2003; Zhou 2005). Such molecular observations are made by including a ds-DNA intercalating dye into the PCR mixture, and monitoring its fluorescence over the course of the reaction (Ririe 1993). This category of dye, which binds between the complementary strands of DNA, can fluoresce only when DNA is in a double-stranded configuration. With adequate dye concentrations, the intensity of its fluorescent signal is proportional to the amount of ds-DNA present. Thus, fluorescence imagery can be used to calculate the amount of ds-DNA present at any point (cycle number and temperature) within the PCR.

Fluorescent dye was first used to observe the increasing concentration of amplified DNA in real-time, by measuring the fluorescence after each extension phase (Higuchi 1993). It was later shown that by continuously monitoring the fluorescence over each cycle, the melting kinetics of the amplicon could also be observed (Ririe 1997). This melting behavior is characterized by a sudden dimming of the fluorescent signal as the dye molecules are systematically quenched with the splitting of the ds-DNA. By plotting this decay versus temperature, characteristic melting curves can be obtained for each sample. By comparing these molecular "fingerprints" with a growing database of melt curve data, no further analyses, such as gel or capillary electrophoresis, are typically needed to identify an amplified PCR product. This DNA melting analysis technology is used in a small number of commercial instruments. With several microliters of sample in a capillary tube, these conventional devices slowly ramp the temperature (~0.2° C./s) while continuously monitoring the fluorescence (Herrmann 2006). This is either performed as an independent analytical process, or following a real-time PCR. This time-dependent DNA melting analysis based on continuous fluorescence acquisition has also been demonstrated on a number of microfluidic systems (Neuzil 2006; Zhang 2006), although independent of the PCR.

To eliminate the time-dependence of the fluorescence acquisition, the cycles and temperatures of the PCR can be spread spatially instead of over time. This can be achieved with continuous-flow PCR (CF-PCR), in which a single microfluidic channel is placed within a steady-state temperature distribution, such that the PCR reagents traveling with a constant flow experience the thermal cycling that induces amplification (Kopp 1998). These channel designs typically have either a serpentine (Obeid 2003; Schnegass 2001) or spiral (Hashimoto 2004) geometry. While the temperature cycling for most CF-PCR devices commonly consists of sharp heating/cooling stages between periodic isothermal dwell times (Li 2006), a recent design has been developed that incorporates steady temperature ramp rates with no cyclic dwell times. Such is achieved by establishing a steady-state thermal gradient across the microfluidic device. An embedded serpentine channel passes periodically with and then against the direction of heat flow, so that the temperature of the pumped fluid cyclically rises and falls through the range of PCR temperatures. Since the activity of the DNA polymerase limits the rate of extension, the channel width in the heating sections is several times larger than in the cooling sections, which allows for slower fluid velocity and thus a lower rate of sample heating. While the traditional CF-PCR geometry allows for the concentration of PCR product to be quantified at each cycle (Nakayama 2006), this recent design has a well-characterized spatial temperature distribution through the transitional temperatures where the amplicon denatures, thus allowing the DNA melting behavior to be characterized. Mao and coworkers (Mao 2002) have demonstrated the concept of spatial DNA melting analysis from a photograph. The thermal gradient PCR device now applies this single acquisition fluorescence detection to rapid PCR, thus making possible the simultaneous amplification, detection, and identification of target DNA fragments.

Therefore, when the microchannel is full, there would be a portion of the sample at each temperature in the cycle as well as each cycle in the process. Therefore, a single fluorescence image taken with an appropriate camera would be able to provide both the amplification and melting data, instantly and simultaneously.

Therefore, disclosed herein is a device for replicating nucleic acid, said device comprising: a microchannel extending from an inlet port to an outlet port; and a heater for producing a spatial temperature gradient. As discussed herein, the microchannel can form one of many patterns over the temperature gradient, including a serpentine pattern. The temperature gradient can be a steady-state gradient. While the temperature can vary across the gradient (i.e., there can be a heating region and a cooling region), the temperature does not vary for a given area on the gradient. In other words, the cooling section stays within a close range, etc. By "steady state" is meant that the temperature within a give region does not vary by more than 0.1, 0.2, 0.4, 0.8, 1.6 or 3.2° C., or any amount in between.

The spatial temperature gradient can vary from one region to another according to the type of PCR reaction being conducted and the nature of the test nucleic acid. For example, the temperature can vary from the heating to the cooling section by 0.2, 0.4, 0.8, 1.6, 3.2, 6.4, 13, or 20° C. or more per millimeter. This refers to the actual thermal gradient in the glass. There can exist a range within any of these numbers, as will be appreciated by one of skill in the art.

A heater or heaters can be used to form the gradient, as described in greater detail below. The heater or heaters can be at the far edges of the device, for example, or can be disposed along a centerline of the microchannel. The device can also comprise a pump for pumping fluid through the microchannel. This is discussed in further detail below.

The temperature gradient across the device is formed by heating a portion of the device surface and cooling a different portion of the surface. The temperature gradient is formed by creating a "path" across the device for heat to travel, along which the temperature will gradually decrease.

Heat can be introduced into the device (heating the device) by contact methods (e.g. electric resistance heaters, heated fluids such as air and water, friction, chemical reactions such as phase change or combustion) and by non-contact methods (e.g. infrared radiation, microwave radiation, solar radiation, ultraviolet radiation, ultrasound).

Heat can be extracted/removed from the device (cooling the device) by passive methods (e.g. natural convection to a cooler fluid such as air or water, conduction to a solid such as a heat sink or fins, radiation away from the surface) and by active cooling methods (e.g. forced convection to a cooler fluid with the use of fans or stirrers, conduction to a thermoelectric cooler). The cooling component can be a conventional refrigeration coil, removing heat from a portion of the temperature gradient.

One embodiment of the invention, which is described in greater detail below, uses a heater or heaters to heat the device down its centerline, and cools the device at the outer edges using fins and/or natural heat convection to air. This embodiment has the highest temperature along the centerline, and the temperature decreasing away toward the edges.

One embodiment of the invention, which is described in greater detail below, uses a heater or heaters to heat the device along one outside edge and cools the device at the opposite outside edge. In this embodiment, the highest temperature is along the heated edge and decreases toward the cooled edge.

The microchannel can comprise various widths, which will accommodate various flow rates through the microchannel, allowing the nucleic acid to spend the appropriate amount of time in each section of the microchannel. For example, the cooling portion of the microchannel can have a width of approximately 30-500 µm, and the heating portion can have a width of approximately 5-5000 µm, or any amount in between. The microchannel can have a depth between 10 and 200 µm. The heating portion can be, for example, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more times greater in width than the cooling portion. Furthermore, the microchannel can have a depth of, for example, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 150, or 200 or more µm. The microchannel can also have a length of about 1, 2, 3, 4, 5, 6, 7, 8, 9, or 10 or more mm, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 250, 500, 1000 or more centimeters. The microchannel can be formed using techniques known to those of skill in the art. For example, Xurography or wet etching can be used. The microchannel can perform any number of amplification cycles. For example, it can perform 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 cycles.

The device can also comprise a light source for emitting light to thereby cause fluorescence. This is discussed in greater detail below. The device can also have a sensor for measuring fluorescence.

Disclosed herein is a device for replicating a nucleic acid, said device comprising: a microchannel; two plates; and a heater; wherein the microchannel is sandwiched between the two plates and the heater is operable to form a spatial temperature gradient across the microchannel. The microchannel can be comprised of a thin film, for example. The device can further comprise at least one fastener for holding the two plates together.

Also disclosed herein is a device for replicating nucleic acid, said device comprising: a channel having a plurality of sections forming a continuous pattern; and a heater disposed along a centerline of the continuous pattern; wherein each section of the channel comprises a first portion and a second portion, the first portion of the channel being narrower than the second portion of the channel.

Disclosed herein is a method of amplifying a nucleic acid, the method comprising the steps of: a) forming a steady state temperature gradient on a device comprising microchannels; and b) exposing a nucleic acid to the temperature gradient in a manner conducive for amplification; thereby amplifying a nucleic acid.

Also disclosed is a method for monitoring nucleic acid replication using a microchip, said method comprising the steps of: a) forming a temperature gradient across a device; and b) exposing a nucleic acid to the temperature gradient in a manner conducive for amplification; and c) detecting nucleic acid amplification using fluorescent monitoring; thereby monitoring nucleic acid amplification using a microchip.

Also disclosed is a method for monitoring nucleic acid replication using a microchip, said method comprising the steps of: a) forming a temperature gradient across a device; and b) exposing a nucleic acid to the temperature gradient in a manner conducive for amplification; while c) detecting nucleic acid amplification using fluorescent monitoring; and d) characterizing the temperature-dependent melting behavior during the denaturing phase of each PCR cycle.

As described above, the device possesses a temperature gradient, through which the amplifying sample travels. The gradient is the primary operational feature of this device. In contrast, previous continuous-flow PCR systems establish 2, 3, or more distinct areas of virtually uniform temperature. Heaters/coolers are placed directly below and/or above the several zones. The PCR chemical reactions are intended to occur during the sample's finite residence time within these isothermal zones. The several isothermal zones are the primary operational features of all other microfluidic continuous-flow PCR devices. The unavoidable gradients that do exist between isothermal zones are treated as a nuisance, and efforts to minimize their effect on the overall PCR system are prevalent in the literature. However, annealing has been shown to not occur at only a single temperature, but over a small range of temperatures. Annealing has been proven to not require a finite residence time, but can be performed by simply heating a sample through the temperature range where annealing occurs. Extension has also been shown to occur over a range of temperatures. It is the time within this range of temperatures, not the time at a single temperature, which characterizes the extension process. Denaturing also does not require a residence time, but occurs virtually instantly. Denaturing occurs over a range of temperatures that is highly dependent on the molecular composition of the DNA. By recognizing the melting behavior of the DNA as the sample passes through the range of temperatures where this melting occurs, the amplifying DNA can be identified. Multi-zone PCR devices inherently neglect these known kinetics of the reaction, and thus settle for a greater amount of complexity.

This device contains a microchannel that meanders through the temperature gradient in a cyclic fashion, such that flowing samples experience the temperature cycling that is not just conducive to PCR, but that is efficiently based around the known reaction kinetics.

In contrast to all other continuous-flow microfluidic PCR devices, this device imposes no mandatory isothermal residence times during the thermal cycling.

In contrast to all other continuous-flow microfluidic PCR devices, all required temperatures for PCR exist within a single thermal zone.

In contrast to all other continuous-flow microfluidic PCR devices, the DNA melting occurs during a gradual temperature ramping of the flowing fluid.

In contrast to single-temperature denaturing zones (all other devices), melting across a spatial temperature gradient allows for observation of the DNA melting transitions, which can be used to identify the amplifying sample.

In contrast to all well-based PCR/melting systems (in which a stationary sample is thermally cycled over time), the thermal gradient PCR device can obtain temperature versus fluorescence DNA melting curves from a single fluorescent snapshot image.

Methods of detecting nucleic acid amplification are well known in the art and are discussed in greater detail below. For example, the nucleic acid can be detected by exposing the nucleic acid to a dye, then detecting interaction of the dye and the nucleic acid. The dye can be fluorescent, such as an intercalating dye. Examples of suitable dyes are discussed in greater detail below, and examples include SYBR Green, LC Green, and LC Green Plus.

Each cycle of nucleic acid replication can be detected, and furthermore, can be imaged to reveal a melting curve. The amount of fluorescence produced by the dye can be measured after each extension. In one example, the information can be provided in "real time." Information related to the denaturing or melting of the nucleic acid can be gathered. More than one nucleic acid sample can be amplified at a time. As discussed below, because melting curve analysis can be conducted on the nucleic acids being amplified, and because most nucleic acids have distinct melting curves, many nucleic acid samples can be distinguished from one another. A DNA melting analysis can differentiate between nucleic acid samples that differ in sequence by only a single base pair, or multiple base pairs. Furthermore, nucleic acids of the same size can be distinguished if the base composition is different, for example if the percent GC content varies by 20, 10, 5, 2, 1 or even less between samples. Additionally, even when the length and base composition are the same, different sequences may have unique melting curves when the nucleic acid sequence is different. Specifically, heterozygous DNA samples can be distinguished from homozygous samples for mutation scanning or genotyping.

Also disclosed is a method of forming a chip with microchannels for use in continuous-flow PCR, said method comprising the steps of: a) creating a digital image of the microchannels using a digital computing machine; b) sending the digital image of the microchannels to a plotting device such that the plotting device forms the microchannels on a thin film; and c) sandwiching the thin film between two plates; thereby forming a chip with microchannels for use in continuous-flow PCR. The digital image of the microchannels can include a serpentine pattern. The method can also include a step of pre-drilling holes in the plates. The method can also include a step of applying pressure to the two plates. The method can also include a step of pre-coating the thin film with an adhesive. The method can also include a step of curing the two plates and the thin film at an elevated temperature. The method can also include a step of forming fluid interconnects in at least one of the two plates. The method can also include a step of forming a spatial temperature gradient. The method can also include a step of pumping a liquid having DNA therein through the microchannels. For example, the liquid can be pumped at a constant volume flow rate. The width of the microchannels can also be varied to control temperature ramping rates.

The above description is general in nature, and more detail of the devices and methods are provided below.

Microfluidic Devices

In numerous embodiments of this invention, the reactions described herein are performed in a microfluidic device. As used herein. "microfluidic device" refers to an apparatus generally comprising a body comprising one or more microscale channels or chambers. In preferred embodiments, such channels are between about 0.1 and 500 µm in at least one cross-sectional dimension (e.g., width or depth). Typically the apparatus of this invention will comprise at least one main channel or chamber, wherein the reactions described herein will occur, as well as one or more side channels, fluidly connected to the at least one main channel or chamber.

Temperature Gradient

In numerous embodiments of this invention, the reaction comprises a thermocyclic reaction. In such embodiments, the main channel is desirably configured to alter the temperature of fluids passing through the channel. Thermal gradients occur naturally as heat dissipates through material. With localized heating, regions in the vicinity of heating elements are hotter, while cooler temperatures exist further from the heat source. When net heat gains are eliminated, a steady state thermal gradient is established. The spatial variance in temperature (linear or higher-order) is a characteristic of the thermal conductivity of the material as well as the arrangement of the several heat sources and drains. Mao et al. have shown that linear thermal gradients can be generated for use with microfluidic chips. Thermal gradients of up to 25° C./mm were shown to be achievable. Cheng et al. used a radial temperature gradient to perform PCR. However, the device was designed such that the PCR sample was only to be shuttled between isothermal regions.

A microfluidic channel running through a spatial temperature gradient was used to perform PCR, using a novel heating platform and a compatible microfluidic chip (Examples 1-3). The critical characteristics of the heating apparatus include the spatial rate of temperature change (° C./mm) and the overall range of temperatures. Features of the microfluidic chip must allow for an adequate number of thermal cycles, fast cooling rates, and moderate heating rates.

The heating of the microfluidic chips is achieved by placing single or multiple heaters against the underside of the microchip. Both "centerline" and "edge" heating have been examined. Centerline heating involves placing a single heater down the middle of the chip. In this configuration, the middle of the chip is at the highest temperature (the denaturing temperature) while the temperature decreases to its coolest point at the outer edges of the chip. Heat dissipates to the atmosphere from all exposed surfaces of the chip. For the edge heating scheme, a single edge is held at a high temperature, while the opposite edge is in contact with a heat sink, through which the majority of the heat is drawn from the chip, thus creating the gradient from one side of the chip to the other. Both types of heating platforms were fabricated out of high temperature polymers (acrylic and/or Teflon), to which the heaters and the microchips were attached.

Figure 17:
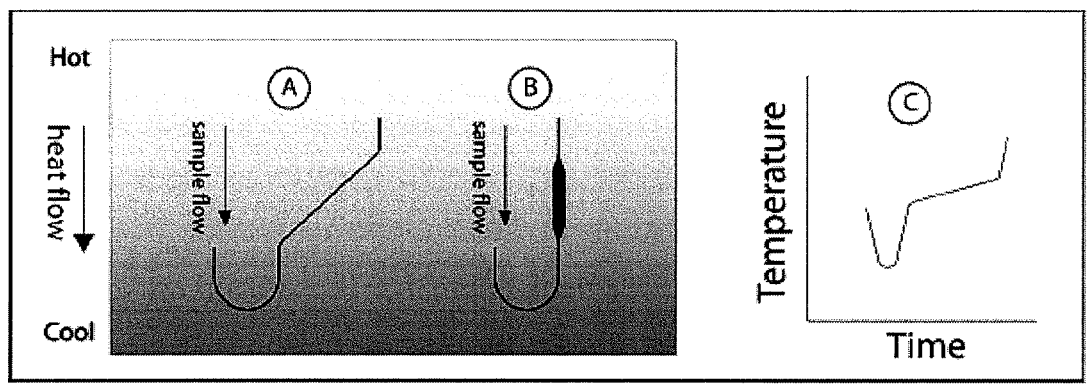
FIG. 17 shows two different methods to generate variable heating and cooling rates from a constant fluid volume flow rate. Microchannels A and B are placed within a spatial temperature gradient. Channel A is laid at varying angles to the direction of the gradient, while channel B has varying cross-sectional area. Fluid passing through both channels exhibit the same temperature profile, which is represented by graph C.
Figure 18:
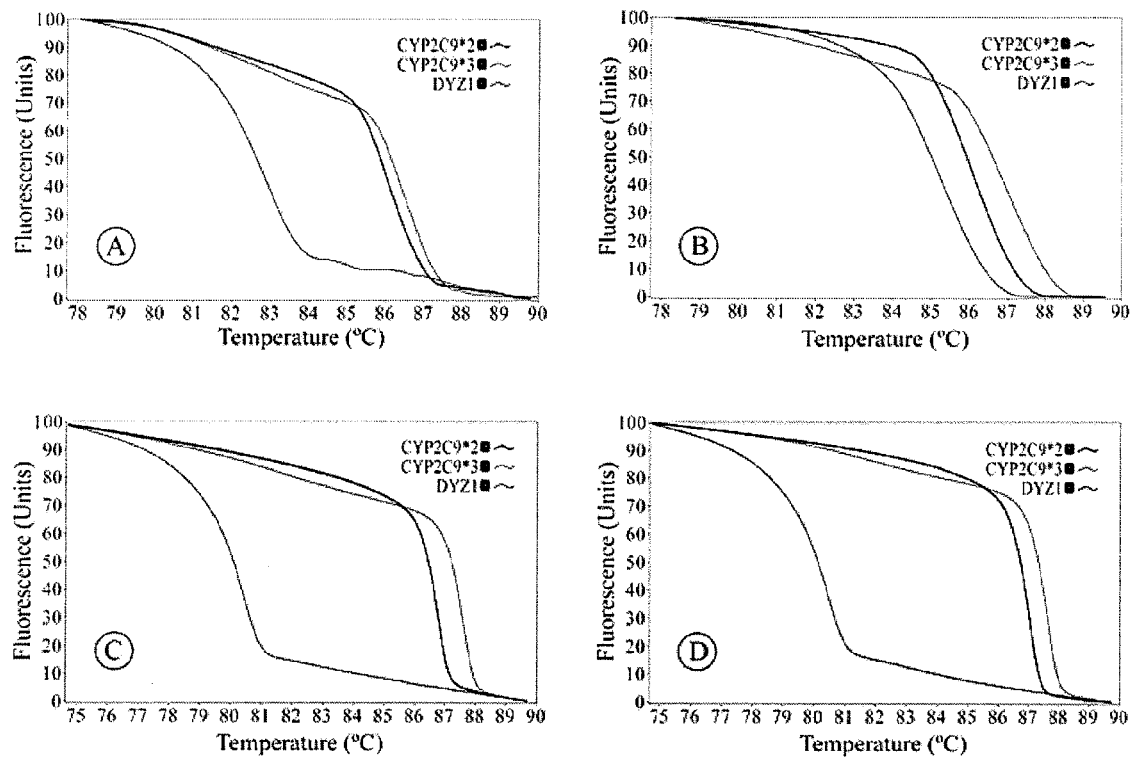
FIG. 18 shows a comparison of DNA melting curves for the three targets. All curves were processed with the Melting Wizard LabVIEW program. A) Spatial melts during amplification on the thermal gradient PCR device. These curves plot the melts shown in FIG. 3. B) Samples were amplified on the LightCycler, and then analyzed with the spatial melting device shown in FIG. 19. C) Samples amplified on the thermal gradient system were melted on the HR-1. These curves were obtained from the 5th elution of each sample. D) Control samples amplified on the LightCycler were then melted on the HR-1.
Figure 19:
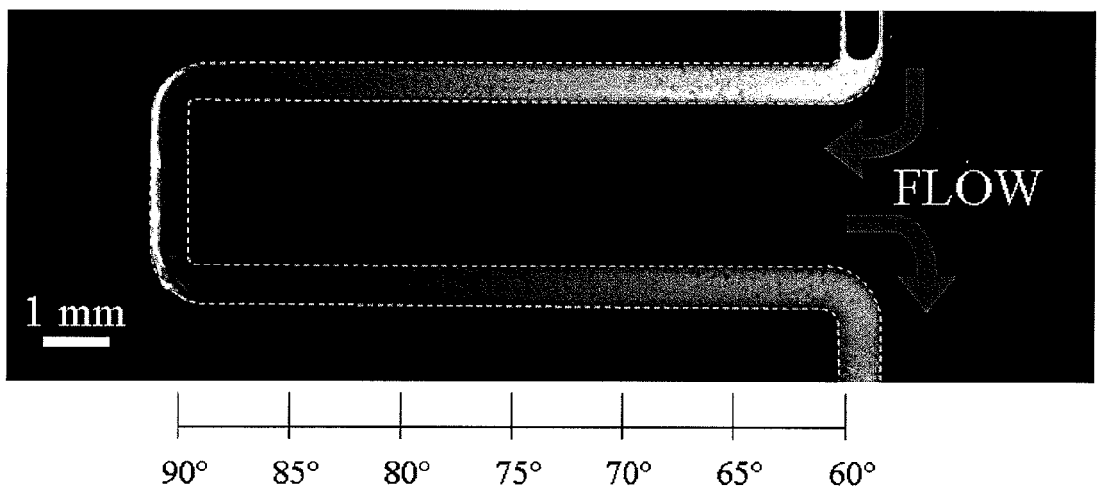
FIG. 19 shows fluorescent image of the spatial melting apparatus. The CYP2C9*3 sample shown in this image was amplified on the LightCycler. The dotted line superimposed on the image outlines the channel.

During PCR cycling, as the sample cools from the denaturation temperature to the annealing temperature, single stranded product begins to form double stranded product, preventing further primer annealing. Therefore, this cooling should be as fast as possible. Since both annealing and denaturing occur nearly instantaneously, the PCR sample should not be held at these temperatures. The heating rate, specifically in the vicinity of the extension temperature, should be moderated according to the size of the product being amplified. Therefore, adapting a linear temperature gradient to an optimum PCR temperature cycle would require either: a) placing the microchannel at different angles in relation to the direction of the gradient, or b) flowing a sample at different velocities within each amplification cycle. This latter result can be achieved by changing the cross-sectional area of the channel within each cycle, as shown in FIG. 17. Li et al. have obtained substantial numerical and experimental data to show the effect of cross-sectional area on fluid velocity.

For reasons of compactness and ease of fabrication, the design of the thermal gradient PCR chip presented here incorporates variations in the channel widths to achieve optimum heating and cooling rates. For simplicity, these designs are such that the channels are wider in the regions where the fluid flow is from the annealing to the denaturing temperatures. Thus, the average heating ramp rate is established by the volume flow rate at the inlet to the device, while the ratio of the heating and cooling rates is determined by the geometry of the channel. In this manner, a constant volume fluid flow rate will produce optimum heating rates combined with rapid cooling.

Figure 2:
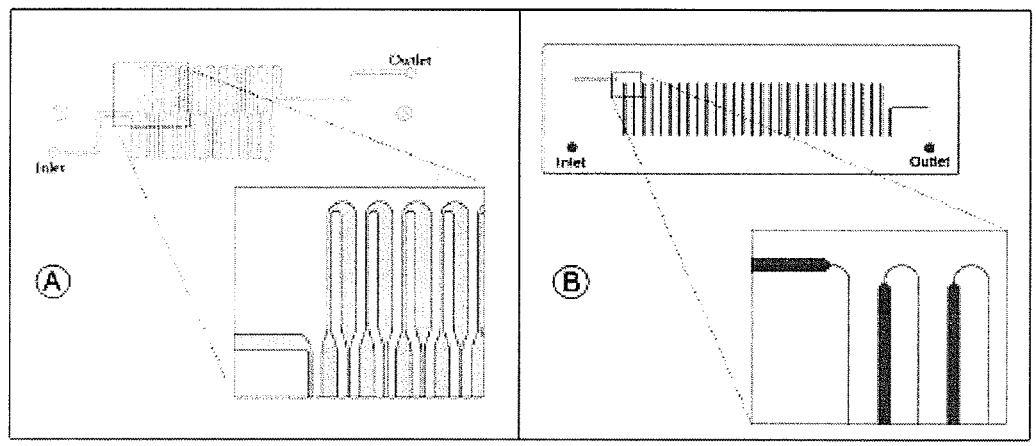
FIG. 2 shows: A) The microfabricated glass chip rests on the two aluminum strips of the heating assembly. Electrical connections to the thin-film heaters beneath both strips are visible. A thermal gradient is induced across the glass by heating one strip (beneath the top edge of the chip, in the image) and drawing heat from the other strip by means of cooling fins. As the PCR mixture travels through the device (from left to right, in the image), it is heated and cooled repeatedly (30× in this particular device). B) The serpentine channel within the chip is located in the region between the strips, where the temperature gradient is virtually linear. The channel is narrow where rapid temperature change is desired and wide where slow ramp rates are needed. C) The etching of the glass produces smooth, curved channel sidewalls.
Figure 3A:
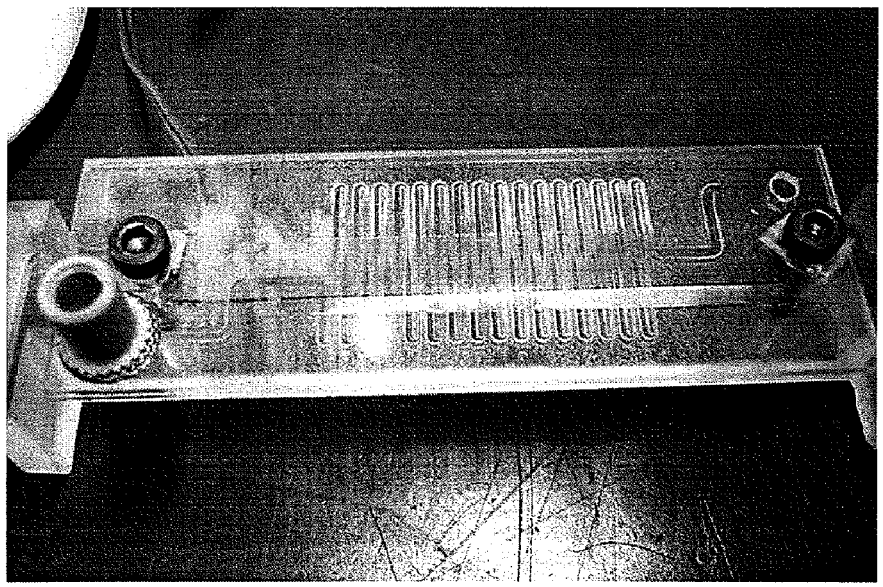
FIG. 3 shows that with the thermal gradient device painted black, the temperature was measured with an IR camera. A) The IR camera generates a 2-D color image displaying temperature. B) Graphing the IR data in a pseudo-3D format allows for visual characterization of the thermal gradient.
Figure 3B:
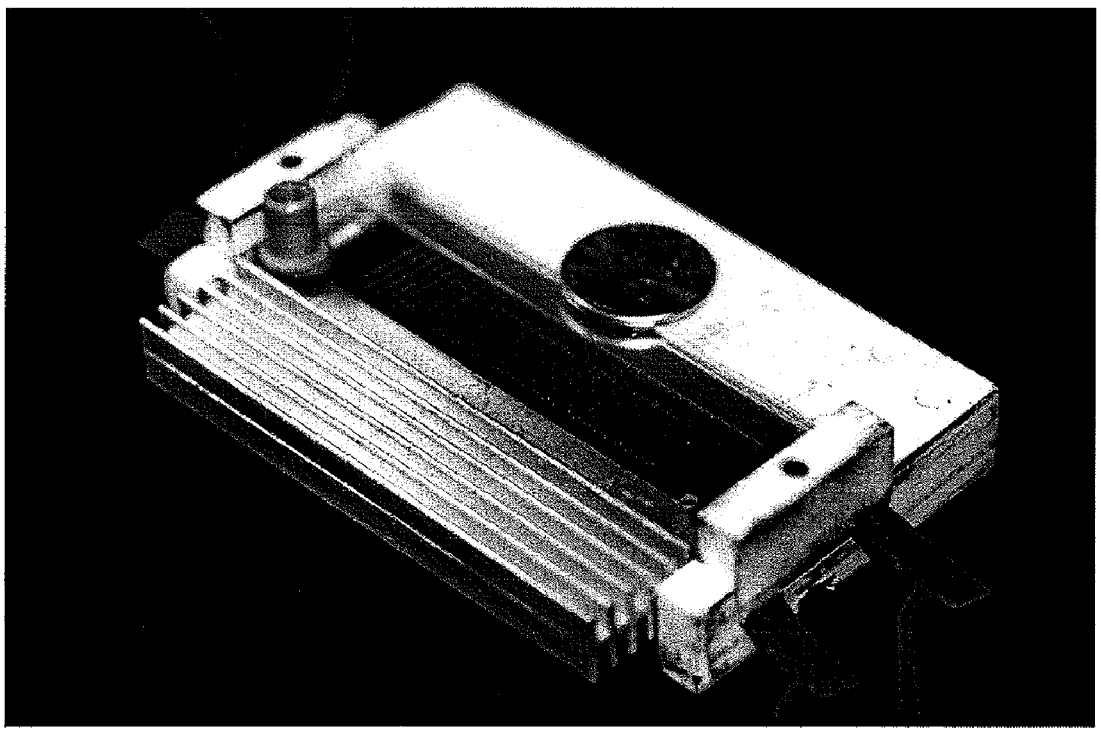
Figure 3C:
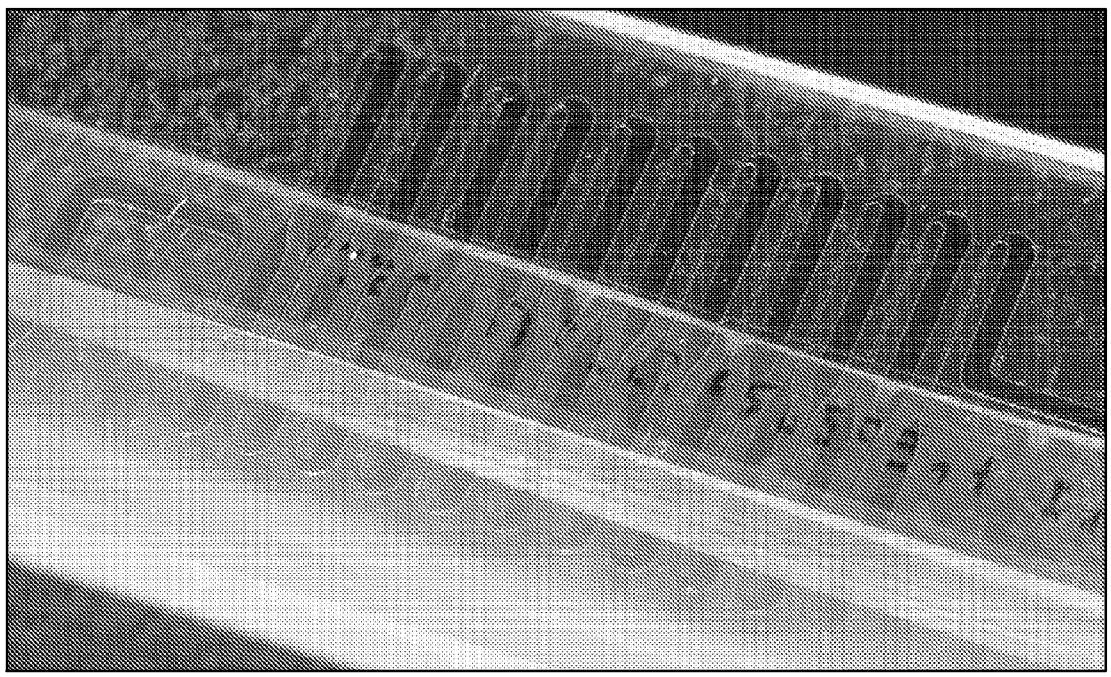
Figure 3D:
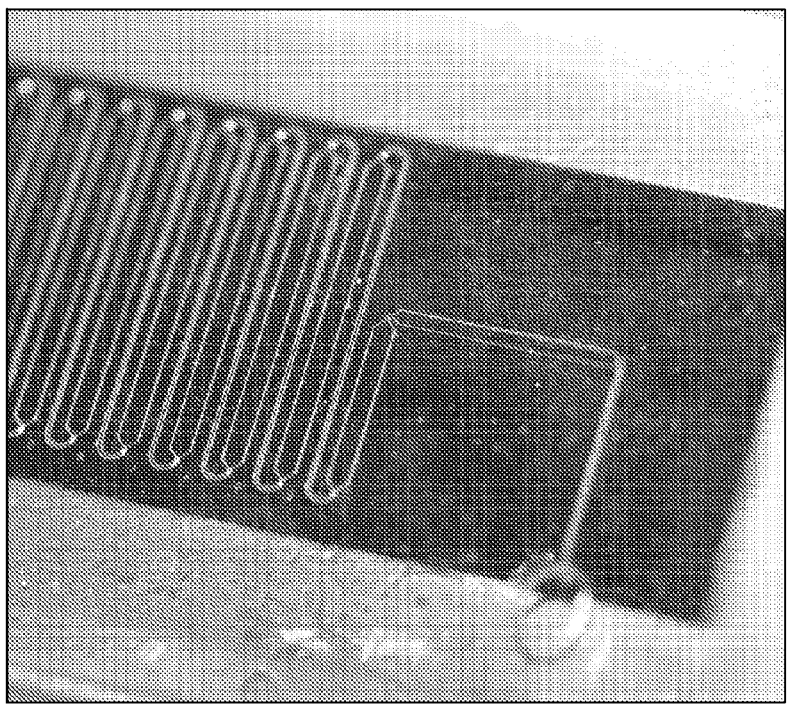
Figure 3E:
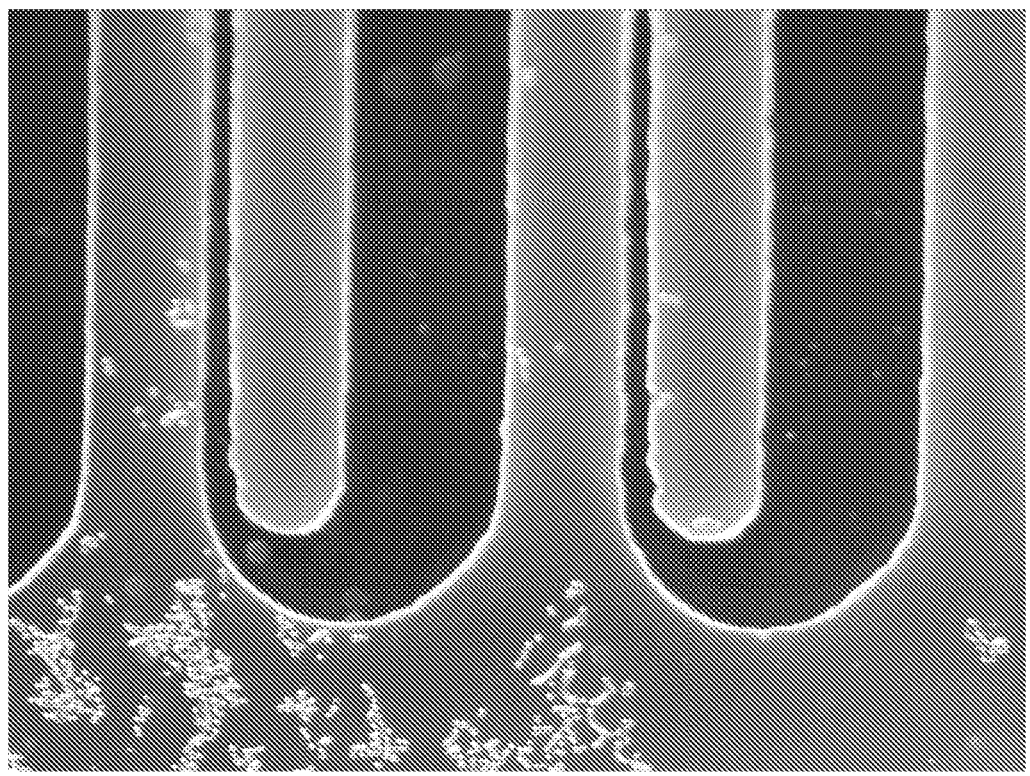
Figure 3F:
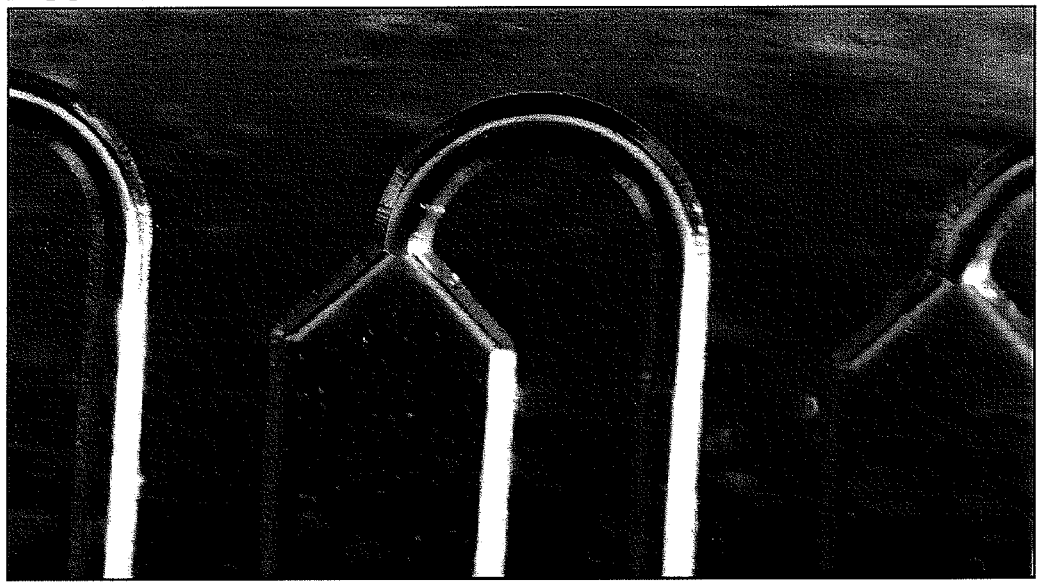

FIG. 2 shows the general designs for both the centerline heating device and the edge heating assembly. For centerline heating, each PCR cycle begins in the narrow channel segment at the center of the chip. The sample rapidly cools as it moves toward the outer edge of the chip. The channel's farthest distance from the center of the chip corresponds to the annealing temperature of the PCR sample. As the channel turns and widens, the sample begins its moderate ramp through the extension temperature and to the denaturing temperature, where the one cycle ends and a successive cycle begins. The PCR chip for edge heating operates the same, only with the denaturing and annealing temperatures being on opposite edges of the chip, as explained previously.

Therefore, with the temperature gradients disclosed herein, distinct temperature regions do not exist, but rather a gradient, in which temperature increases/decreases gradually over the course of the chip. By "gradually" is meant that there is a continual change in temperature across the chip, as compared to distinct temperature zones. The "change in temperature" does not mean that the temperature changes at a given point, but rather is held steady at a given point and changes across the entire chip. The difference between a graduated chip and a chip with various zones can be seen, for example, in FIG. 15.

PCR Protocols

Cyclic polymerase-mediated reactions such as PCR comprise three overlapping processes: denaturation, primer annealing, and primer extension. For certain reactions, including PCR, such processes are carried out at least 2, and generally 3, or occasionally more than 3, different temperatures. Methods of determining and carrying out such temperatures are well known to those of skill in the art. For example, denaturation steps are often performed at 95° to 98° C. Such temperatures will often be used to carry out the present invention. Also, numerous protocols teach the performance of an initial, long denaturation step, particularly when using complex nucleic acids as a starting template, e.g. genomic DNA. In certain embodiments, the present invention will include such initial, longer denaturation steps.

The second process of a cyclic polymerase-mediated reaction is the annealing step, when a primer is hybridized to a denatured template molecule. As known to those of skill, optimal annealing temperatures depend on the melting temperature for the primer and templates, typically falling in the range from about 40° C. to about 65° C. Numerous methods of varying simplicity and precision are known to calculate the melting temperature of nucleic acids. Any such method can be used in the present invention.

Optimal temperatures for the extension step of a PCR are also extensively taught in the prior art. Generally, this temperature is between about 70° C. and about 80° C. Often, the temperature of 72° C. is cited as the ideal temperature for extension. Other temperatures may, however, be used, e.g., depending on the polymerase used, or when performing a PCR wherein the annealing and extension steps are performed simultaneously, as described infra. In such cases, it may be desirable to perform the single annealing/extension step at a temperature intermediate to the ideal temperature for each individual process.

Reagents for the practice of PCR and related reactions are amply described in the prior art. For example, Innis, Sambrook, and Ausubel, all supra, each provide substantial teaching regarding optimal reagents for PCR. In addition, numerous references on the Internet provide protocols and methods for PCR and related reactions (see, for example, www.alkami.com/or www.promega.com/amplification/prodguide/).

Buffers for PCR and related reactions can be easily made using standard laboratory chemicals according to recipes provided in the above-cited protocols. Alternatively, buffers and additional reagents useful for PCR can be commercially obtained from any of a variety of companies such as BRL, Sigma, Perkin-Elmer, Roche, Boehringer Mannheim, Stratagene, NEB, and others. Such companies and the above references provide substantial guidance for the optimal use of such buffers. Nucleoside triphosphates, often derivatized as described infra, can also be readily obtained commercially. In addition, guidance for their use can be found in any of a multitude of sources including guides such as Innis, Sambrook, Ausubel, etc., product literature from companies, Internet protocols and technical discussion groups, etc. Similarly, other reagents commonly used in cyclic polymerase-mediated reactions such as $Mg^{++}$ ions, BSA, detergents, etc, can be readily obtained and guidance for their optimal use readily found in any of the above sources.

The templates used in the methods of this invention can be obtained from any source that potentially contains an amplifiable nucleic acid. Such sources include those from any animal, including humans and other mammals, as well as plants, fungi, bacteria, and archaebacteria. Templates can be prepared from any material containing cells or nucleic acids. In the case of an animal, such material includes, e.g. tissue biopsy, blood, hair, buccal scrapes, etc. In the case of plants, such materials include seeds, spores, embryos, flowers, ovules, leafs, stems, etc. Methods for the preparation of templates can be found in a multitude of sources, including Innis, Sambrook, Ausubel, all supra. Any such method can be used in the present invention. Typically, these methods involve cell lysis, followed by purification of nucleic acids by methods such as phenol/chloroform extraction, electrophoresis, and/or chromatography. Often, such methods include a step wherein the nucleic acids are precipitated, e.g. with ethanol, and resuspended in an appropriate buffer for addition to a PCR or similar reaction.

The choice of the template used in the present invention will depend on the particular application used. Any of a large number of such applications exist. Simply put, any nucleic acid desirably amplified may be used in the present invention. Such applications include diagnostic procedures, wherein the presence or absence of a particular nucleic acid provides information regarding the existence or state of a biological condition, such as a disease. In other applications, nucleic acids are amplified for use in a downstream application, such as for use as a probe, or for sequencing, i.e. to determine the precise sequence of a particular genetic locus in one or more individual samples.

In certain embodiments, a plurality of templates from one or more sources are used in the present invention. For example, a single nucleic acid from a multitude of sources may be amplified to screen for the presence or absence of a particular sequence. In other applications, a plurality of nucleic acids may be amplified from a single sample or individual, thereby allowing the assessment of a variety of nucleic acids in a single individual, e.g. to simultaneously screen for a multitude of disease markers in an individual. Any of the above applications can be easily accomplished using the apparatus and integrated systems described herein. For example, in one embodiment, an apparatus comprising a plurality of sources of test samples is used to carry out the present invention.

Oligonucleotides for use as primers, e.g., in PCR or non-thermal amplification reactions, are typically synthesized chemically according to the solid phase phosphoramidite triester method described by Beaucage and Caruthers (1981). *Tetrahedron Letts.*, 22(20):1859-1862, e.g., using an automated synthesizer, as described in Needham-VanDevanter et al. (1984) *Nucleic Acids Res.*, 12:6159-6168. Oligonucleotides can also be custom made and ordered from a variety of commercial sources known to persons of skill. Purification of oligonucleotides, where necessary, is typically performed by either native acrylamide gel electrophoresis or by anion-exchange HPLC as described in Pearson and Regnier (1983) *J. Chrom.* 255:137-149. The sequence of the synthetic oligonucleotides can be verified using the chemical degradation method of Maxam and Gilbert (1980) in Grossman and Moldave (eds.) Academic Press, New York, *Methods in Enzymology* 65:499-560.

While primers can hybridize to any of a number of sequences, selecting optimal primers is typically done using computer assisted consideration of available sequences and excluding potential primers which do not have desired hybridization characteristics, and/or including potential primers which meet selected hybridization characteristics. This is done by determining all possible nucleic acid primers, or a subset of all possible primers with selected hybridization properties (e.g., those with a selected length, G:C ratio, uniqueness in the given sequence, etc.) based upon the known sequence. The selection of the hybridization properties of the primer is dependent on the desired hybridization and discrimination properties of the primer. In general, the longer the primer, the higher the melting temperature. As noted above, any desired primer can be synthesized using standard methods. In one aspect, microfluidic systems for, e.g. PCR, include pre-made primer sets which are selected for use in the system.

Microfluidic systems utilizing primer sets for, e.g., PCR, are set forth in WO 98/45481. For example, modular primers can be used in the reactions of this invention. See, WO 98/45481 and Beskin et al. (1995) *Nucleic Acids Research* 23(15):2881-2885. See, also, Raja et al. (1997) *Nucleic Acids Research* 25(4):800-805.

In general, it is expected that one of skill is thoroughly familiar with the theory and practice of nucleic acid hybridization and primer selection. Gait, ed. *Oligonucleotide Synthesis: A Practical Approach*, IRL Press, Oxford (1984), W. H. A. Kuijpers *Nucleic Acids Research* 18(17), 5197 (1994); K. L. Dueholm *J. Org. Chem.* 59, 5767-5773 (1994); S. Agrawal (ed.) *Methods in Molecular Biology*, volume 20; and Tijssen (1993) *Laboratory Techniques in biochemistry and molecular biology-hybridization with nucleic acid probes*, e.g., part 1 chapter 2 "overview of principles of hybridization and the strategy of nucleic acid probe assays", Elsevier, N.Y. provide a basic guide to nucleic acid hybridization. Innis supra provides an overview of primer selection.

One of skill will recognize that the 3' end of an amplification primer is more important for PCR than the 5' end. Investigators have reported PCR products where only a few nucleotides at the 3' end of an amplification primer were complementary to a DNA to be amplified. In this regard, nucleotides at the 5' end of a primer can incorporate structural features unrelated to the target nucleic acid; for instance, in one embodiment, a sequencing primer hybridization site (or a complement to such as primer, depending on the application) is incorporated into the amplification primer, where the sequencing primer is derived from a primer used in a standard sequencing kit, such as one using a biotinylated or dye-labeled universal M13 or SP6 primer.

One of skill will recognize that there are a variety of possible ways of performing the primer selection steps, and that variations on the steps are appropriate. Most typically, selection steps are performed using simple computer programs to perform the selection as outlined above; however, all of the steps are optionally performed manually. One available computer program for primer selection is the MacVector program from Kodak. An alternate program is the MFOLD program (Genetics Computer Group, Madison Wis.) which predicts secondary structure of, e.g., single-stranded nucleic acids. In addition to programs for primer selection, one of skill can easily design simple programs for any or all of the preferred selection steps.

Any of a variety of polymerases can be used in the present invention. For thermocyclic reactions, the polymerases are thermostable polymerases such as Taq, KlenTaq, Stoffel Fragment, Deep Vent, Tth, Pfu, Vent, and UlTma, each of which are readily available from commercial sources. Similarly, guidance for the use of each of these enzymes can be readily found in any of a number of protocols found in guides, product literature, the Internet (see, for example, www.alkami.com/), and other sources.

Those of skill in the art are aware of the variety of nucleotides available for use in the present reaction. Typically, the nucleotides will consist at least in part of deoxynucleotide triphosphates (dNTPs), which are readily commercially available. Parameters for optimal use of dNTPs is also known to those of skill, and is described, e.g. in Innis, Sambrook, or Ausubel, supra. In addition, a large number of nucleotide derivatives are known to those of skill and can be used in the present reaction. Such derivatives include fluorescently labeled nucleotides, allowing the detection of the product including such labeled nucleotides, as described below. Also included in this group are nucleotides that allow the sequencing of nucleic acids including such nucleotides, such as dideoxynucleotides and boronated nuclease-resistant nucleotides, as described below. Other nucleotide analogs include nucleotides with bromo-, iodo-, or other modifying groups, which groups affect numerous properties of resulting nucleic acids including their antigenicity, their replicatability, their melting temperatures, their binding properties, etc. In addition, certain nucleotides include reactive side groups, such as sulfhydryl groups, amino groups, N-hydroxysuccinimidyl groups, that allow the further modification of nucleic acids comprising them.

Detection of Nucleic Acids

In one class of embodiments of this invention, a detectable label is incorporated into a nucleic acid during at least one cycle of the reaction. Such labels can be detected by spectroscopic, photochemical, biochemical, immunochemical, electrical, optical or chemical means. Useful labels in the present invention include fluorescent dyes (e.g., fluorescein isothiocyanate, Texas red, rhodamine, and the like), radiolabels (e.g., $^3$H, $^{125}$I, $^{35}$S, $^{14}$C, $^{32}$P, $^{33}$P, etc.), enzymes (e.g., horseradish peroxidase, alkaline phosphatase etc.) colorimetric labels such as colloidal gold or colored glass or plastic (e.g. polystyrene, polypropylene, latex, etc.) beads. The label is coupled directly or indirectly to a component of the assay according to methods well known in the art. As indicated above, a wide variety of labels are used, with the choice of label depending on sensitivity required, ease of conjugation with the compound, stability requirements, available instrumentation, and disposal provisions. Non-radioactive labels are often attached by indirect means.

Polymerases can also incorporate fluorescent nucleotides during synthesis of nucleic acids. See, e.g. Hawkins et al., U.S. Pat. No. 5,525,711, where the use of pteridine nucleotide analogs which are incorporatable by Taq is described.

The term "double stranded DNA dye" used herein refers to a fluorescent dye that (1) is related to a fragment of DNA or an amplicon and (2) emits at a different wavelength in the presence of an amplicon in duplex formation than in the presence of the amplicon in separation. A double stranded DNA dye can be a double stranded DNA intercalating dye or a primer-based double stranded DNA dye.

A double stranded DNA intercalating dye is not covalently linked to a primer, an amplicon or a nucleic acid template. The dye increases its emission in the presence of double stranded DNA and decreases its emission when duplex DNA unwinds. Examples include, but are not limited to, ethidium bromide, YO-PRO-1, Hoechst 33258, SYBR Gold, and SYBR Green I. Ethidium bromide is a fluorescent chemical that intercalates between base pairs in a double stranded DNA fragment and is commonly used to detect DNA following gel electrophoresis. When excited by ultraviolet light between 254 nm and 366 nm, it emits fluorescent light at 590 nm. The DNA-ethidium bromide complex produces about 50 times more fluorescence than ethidium bromide in the presence of single stranded DNA. SYBR Green I is excited at 497 nm and emits at 520 nm. The fluorescence intensity of SYBR Green I increases over 100 fold upon binding to double stranded DNA against single stranded DNA. An alternative to SYBR Green I is SYBR Gold introduced by Molecular Probes Inc. Similar to SYBR Green I, the fluorescence emission of SYBR Gold enhances in the presence of DNA in duplex and decreases when double stranded DNA unwinds. However, SYBR Gold's excitation peak is at 495 nm and the emission peak is at 537 nm. SYBR Gold reportedly appears more stable than SYBR Green I. Hoechst 33258 is a known bisbenzimide double stranded DNA dye that binds to the AT rich regions of DNA in duplex. Hoechst 33258 excites at 350 nm and emits at 450 nm. YO-PRO-1, exciting at 450 nm and emitting at 550 nm, has been reported to be a double stranded DNA specific dye. In a preferred embodiment of the present invention, the double stranded DNA dye is SYBR Green I.

A primer-based double stranded DNA dye is covalently linked to a primer and either increases or decreases fluorescence emission when amplicons form a duplex structure. Increased fluorescence emission is observed when a primer-based double stranded DNA dye is attached close to the 3' end of a primer and the primer terminal base is either dG or dC. The dye is quenched in the proximity of terminal dC-dG and dG-dC base pairs and dequenched as a result of duplex formation of the amplicon when the dye is located internally at least 6 nucleotides away from the ends of the primer. The dequenching results in a substantial increase in fluorescence emission. Examples of these type of dyes include but are not limited to fluorescein (exciting at 488 nm and emitting at 530 nm), FAM (exciting at 494 nm and emitting at 518 nm), JOE (exciting at 527 and emitting at 548), HEX (exciting at 535 nm and emitting at 556 nm), TET (exciting at 521 nm and emitting at 536 nm), Alexa Fluor 594 (exciting at 590 nm and emitting at 615 nm), ROX (exciting at 575 nm and emitting at 602 nm), and TAMRA (exciting at 555 nm and emitting at 580 nm). In contrast, some primer-based double stranded DNA dyes decrease their emission in the presence of double stranded DNA against single stranded DNA. Examples include, but are not limited to, fluorescein (exciting at 488 nm and emitting at 530 nm), rhodamine, and BODIPY-FI (exciting at 504 nm and emitting at 513 nm). These dyes are usually covalently conjugated to a primer at the 5' terminal dC or dG and emit less fluorescence when amplicons are in duplex. It is believed that the decrease of fluorescence upon the formation of duplex is due to the quenching of guanosine in the complementary strand in close proximity to the dye or the quenching of the terminal dC-dG base pairs.

The term "n" used herein refers to the total number of nucleic acid templates that can be amplified and quantified by applying the methods as described in the present invention. When only one double stranded DNA dye is added to a PCR mixture, n is an integer and "n" is 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40. If emission of various double stranded DNA dyes does not overlap, it is contemplated within the scope of this invention that more than one double stranded DNA dye can be used in a single PCR mixture. For example, a number of primer-based double stranded DNA dyes can be combined in a single PCR reaction or can be further combined with a double stranded DNA intercalating dye, as long as these dyes emit at different wavelengths. However, two double stranded DNA intercalating dyes may not be combined in a single PCR mixture. When x number of dyes are combined in a single PCR mixture, where x is an integer and x is greater than or equal to 2, it is contemplated that the total number of nucleic acid templates in a single PCR reaction is an integer and 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40.

The term "melting temperature" or "Tm" refers to the temperature at which 50% of a given amplicon is in the double stranded conformation and 50% is in the single stranded conformation. Tm of any given DNA fragment or amplicon can be determined by methods well known in the art. For example, one method in the art to determine a Tm of a DNA fragment or an amplicon is to use a thermostatic cell in an ultraviolet spectrophotometer and measure absorbance at 268 nm as temperature slowly rises. The absorbance versus temperature is plotted, presenting an S-shape curve with two plateaus. The absorbance reading half way between the two plateaus corresponds to the Tm of the fragment or amplicon. Alternatively, the first negative derivative of the absorbance versus temperature is plotted, presenting a normal distribution curve. The peak of the normal curve corresponds to the Tm of the fragment or amplicon.

A calculation method commonly known as the nearest neighbor method can be used to determine the Tm of an amplicon. The nearest neighbor method takes into account the actual sequence of the amplicon, its length, base composition, salt concentration, entropy, and concentration.

Furthermore, the Tm of an amplicon or Tms of multiple amplicons can be first determined by the nearest neighbor method and fine tuned or accurately determined in the presence of a double stranded DNA dye in a single PCR reaction. For example, a thermostable polymerase, nucleic acid templates for an amplicon or multiple amplicons, primers for the amplicons, a double stranded DNA dyes like SYBR Green I, and other necessary reagents are placed in a single PCR mixture. The PCR mixture is thermally cycled to amplify the amplicons for a number of cycles between a total denaturing temperature, an annealing temperature and/or an extension temperature. At the end of the PCR cycles, the mixture is heated from the annealing or extension temperature to the total denaturing temperature at a rate of 0.01° C.–3° C. per second. At the same time, the mixture is illuminated with light at a wavelength absorbed by the dye and the dye's emission is detected and recorded as an emission reading. The first negative derivative of the emission reading with respect to temperature is plotted against temperature to form a number of normal curves, and each peak of the curve corresponds to the actual Tm of an amplicon in the PCR reaction.

The emission of a double stranded DNA dye is obtained, detected or recorded cycle by cycle in a PCR reaction after a PCR mixture is illuminated or excited by light with a wavelength absorbed by the dye. The term "cycle by cycle" refers to measurement in each cycle. The emission reading at a measuring temperature is taken to calculate the emission amount of an amplicon in a cycle. It is contemplated that emission can be detected, recorded, or obtained continuously or intermittently.

In a continuous recording process, the emission of the double stranded DNA dye is monitored and recorded, for example, every 50 ms, every 100 ms, every 200 ms or every 1 s, in each cycle of a PCR reaction. A three dimensional plot of time, temperature and emission can be formed. In any given cycle, the emission reading at a time point that corresponds to a desired MT (melting temperature) is taken to determine the emission amount of the amplicon in the cycle.

In an intermittent recording process, the emission reading is taken only when the reaction temperature reaches a desired MT in each cycle. In a preferred embodiment, when a measuring temperature is reached, the PCR reaction is kept at the MT for 0.5 s to 20 s, preferably 1 s to 10 s; the emission reading is obtained, measured or recorded thereafter; and the temperature continues to rise in the PCR reaction.

The term "pre-Tm emission" refers to the emission reading measured, recorded or obtained at a pre-Tm MT. The term "post-Tm emission" refers to the emission reading measured, recorded or obtained at a post-Tm MT.

The difference between a pre-Tm emission and a post-Tm emission represents an emission amount of the amplicon with the Tm in a cycle. The emission amount of an amplicon reflects the change of the amplicon from duplex to separation. For example, when a pre-Tm emission is measured at a pre-Tm MT at which 99% of an amplicon is in duplex and a post-Tm emission is measured at a post-Tm MT at which 99% of the amplicon is in separation, the difference represents close to 100% of the emission of the amplicon in duplex. By the same token, when a pre-Tm emission is measured at a measuring temperature at which 75% of an amplicon is in duplex and a post-Tm emission is measured at a post-Tm MT at which 75% of the amplicon is in separation (25% in duplex), the difference represents close to 50% of the emission of the amplicon in duplex.

Cycle-by-cycle monitoring for real time PCR is usually obtained over the time course of the reaction. That is, if each cycle takes 60 s, one recording is taken each 60 s, and the data for a 30-cycle amplification is obtained over a 30 min period. However, continuous flow PCR provides an opportunity for multiple cycles to be separated in space rather than time. From one photograph, multiple cycles of PCR are imaged, and the pre-Tm fluorescence density of the channel at each cycle is directly related to the amount of PCR product present at each cycle. That is, along one isothermal (pre-Tm) line of an image or photograph, the fluorescence density or brightness at each cycle is quantified by image analysis or scanning. This brightness is directly related to the amount of PCR product present at each cycle. If this fluorescence is plotted against cycle number, the fluorescence growth curves of real-time PCR are obtained, as are well known in the art. This provides a simple means of determining the initial copy number of template—if fluorescence appears at a low cycle number, the initial concentration was high, if it appears at a high cycle number, the initial concentration was low. Standard curves can be used to quantify this inverse log relation, as is well known for real-time PCR. The advantage of spatial vs time acquisition is that all real-time data can be extracted from all cycles at one time point, i.e., from one photograph or image.

In addition to real-time data, the methods and devices of the invention enable the construction of and comparison of molecular melt curves. Molecular melt curves are alternatively described as "thermal melting curves", "thermal melt curves", "thermal property curves", "thermal denaturation curves" or "thermal profile curves." Accordingly, an analysis involving the generation of molecular melt curve can also be described as a molecular melt analysis, a thermal melting analysis, a thermal melt analysis, a thermal property analysis, a thermal denaturation analysis, or a thermal profile analysis. In such an analysis, a sample of a target molecule, or target molecules, to be tested is flowed into one or a number of microchannels in a microfluidic device. Optionally, the target molecule is then contacted with one or more test molecules that are screened for possible binding capability with the target molecule and/or with an indicator such as a fluorescence indicator dye or molecule. Optional embodiments of the present invention allow for multiple configurations of, e.g., heat application, flow speed, reagent composition, binding conditions, and timing of all the multiple variants involved.

Once the test molecule interacts with the target molecule and/or labeling compound, the present invention sets the reaction conditions, in a controllable manner, to a desired temperature (either continuously over a range of temperatures or non-continuously to discrete temperature points). Selected physical properties of the molecules are measured in the microfluidic device and thermal property curves produced from the measurements. The thermal property curves are based upon, e.g., the temperature induced denaturation or unfolding that occurs when the molecules are subjected to heat. Denaturation can include, e.g., loss of secondary, tertiary, or quaternary structure by means of uncoiling, untwisting, or unfolding, disassociation of nucleic acid strands, etc.

Methods of Making the Devices

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

An appropriate temperature gradient can be achieved through a glass or a plastic chip by heating the chip either along one edge or down the centerline. By pumping fluid through a serpentine channel fabricated within the chip, the flowing sample is heated and cooled rapidly. Since cooling from the high temperature to the low should be as fast as possible, the width of the channel in those regions has been designed to be as thin as the fabrication process will allow. The ramp rate from the annealing temperature to the extension temperature should be slow enough to allow for full extension of the DNA polymerase. Therefore, the channels are wider in these regions. In an alternative embodiment, the channels can also be narrower in these regions.

Figure 13:
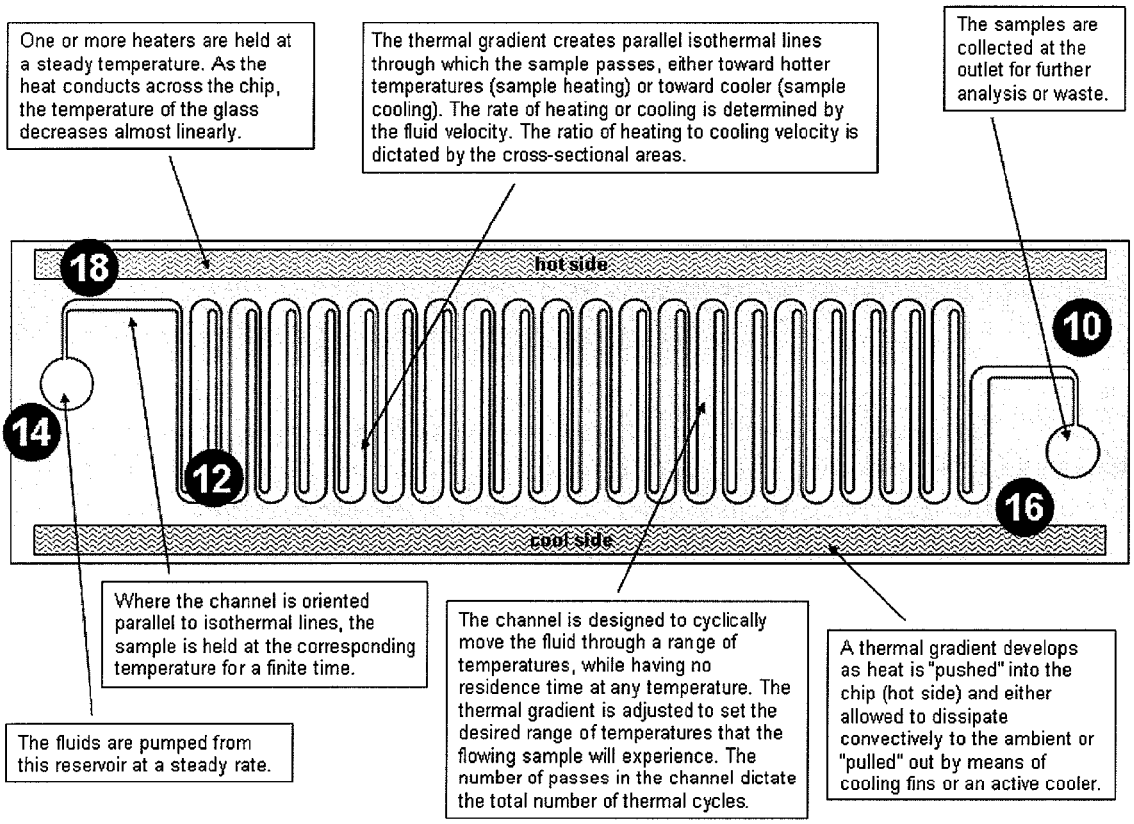
FIG. 13 shows that the continuous flow thermal gradient device described herein is capable of performing fluorescent analysis.

Referring now to FIG. 13, there is shown a schematic representation of an embodiment of the present disclosure. A microchip 10 includes a channel 12 extending from an inlet port 14 to an outlet port 16. As can be observed, the channel 12 forms a serpentine pattern as it extends from the inlet port 14 to the outlet port 16. A heater 18 is located adjacent the channel 12. As will be explained in more detail below, the heater 18 forms a spatial temperature gradient across the chip 10. It will be noted that the width of the channel 12 is narrower as the fluid inside of the channel 12 flows away from the heater 18. This causes the fluid to rapidly cool. As the fluid inside of the channel 12 moves toward the heater, the channel is wider. This allows the fluid to heat at an appropriate rate. It will be appreciated that where the channel 12 is narrow, the fluid inside of the channel 12 moves more rapidly. Where the channel 12 is wider, the fluid moves more slowly.

It will be appreciated that the spatial temperature gradient formed by the heater 18 forms three heat zones conducive to denaturing, annealing, and extension. The denaturing zone is closest to the heater 18 since it requires the highest temperature (for example, 80-95 degrees Celsius). The annealing zone is farthest from the heater 18 since it requires the lowest temperature (for example, 40-62 degrees Celsius). The extension zone is located between the denaturing zone and the annealing zone since it requires an intermediate temperature (for example, 60-78 degrees Celsius).

The serpentine nature of the channel 12 allows for cycling or amplification of the PCR process. Thus, DNA inside of the channel 12 may be replicated several times as it is heated and cooled repeatedly while traveling through the channel 12 through the three (3) temperatures required for denaturing, annealing and extension. The amplified DNA maybe collected in the outlet port 16.

In one exemplary embodiment, a continuous-flow PCR chip according to the present disclosure is made from a thin film using Xurography. Xurography uses a knife plotter with a very fine blade to trace out a pattern on a thin film. In the present case, the pattern is the channel. Using Xurography, a digital image of a desired channel is first created on a computer. This may be done using Adobe® Illustrator® or any other suitable program for designing images in a digital format. Next, a file containing the finished image is sent to a plotter, such as a knife plotter, that uses a cutting instrument, such as a fine blade, to trace out the channel pattern in a thin film. Once the channel has been formed, the thin film is then placed between two plates, such as glass or plastic plates. The plates, with the thin film sandwiched in between, is then cured.

Using this procedure, a single thermal gradient chip can be fabricated in less than 45 minutes (including curing time). Although considered disposable, chips fabricated in this 15 manner have been used to amplify more than PCR samples before eventual failure.

In one exemplary embodiment, the depth of the channel is approximately 25 µm, the width of the channel in a cooling portion of the channel is in the range of approximately 150 to 250 µm, the width of the channel in a heating portion of the channel is in the range from approximately 500-1000 µm. The number of amplification cycles is approximately 22, and the total length of the channel is approximately 30 centimeters.

It will be appreciated that the above dimensions may vary depending on the needs of the users. By creating a chip in the manner described herein, additional data can be obtained that was not previously possible. The PCR samples amplified in a chip built in accordance with the present disclosure typically contains a unique fluorescent dye. A characteristic of this type of dye (SYBR Green, LC Green, LC Green Plus, etc.) is that, when excited by the appropriate wavelength of light, the fluorescence is emitted only when the DNA is in a double stranded configuration. By measuring the amount of fluorescence at the end of the extension phase of each cycle, the amount of PCR amplicon being produced can be observed as the process develops. In addition, monitoring the fading of the signal as the sample approaches the denaturing temperature provides specific information about the size and some information about the sequence of the DNA in the sample.

Assuming that a PCR mixture fills the serpentine channel of the device, there would be a portion of the sample at each temperature in the cycle as well as each cycle in the process. Therefore, a single fluorescence image taken with an appropriate camera would be able to provide both the amplification and melting data, instantly and simultaneously.

The PCR product could then be collected at the outlet of the chip for additional analysis or disposal.

Figure 14:
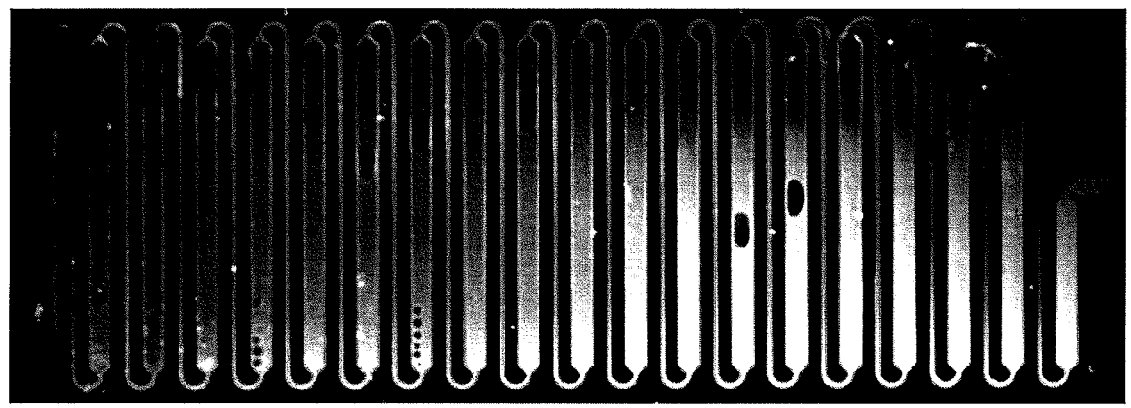
FIG. 14 shows a fluorescent image showing cycles 12 through 30 of a 30-cycle chip. As in FIG. 13, the edge of the chip that corresponds to the top edge of this image is kept hot and the opposite edge (the bottom) is kept cooler.

Referring now to FIG. 14, there is shown another exemplary embodiment of the present disclosure. In this embodiment, there is shown a serpentine channel having a plurality of sections. Although not shown, a heating element may be placed down the centerline of the serpentine channel. As can be observed, each section of the channel comprises a narrow portion and a wide portion. The narrow portion of the channel allows for rapid cooling. The wide portion of the channel allows for slow heating. In this manner, the channel shown in FIG. 14 allows for a sample to pass through all three temperature zones required for PCR to be accomplished.

EXAMPLES

Example 1

Continuous-Flow Thermal Gradient PCR

Continuous-flow thermal gradient PCR is a new DNA amplification technique that is characterized by periodic temperature ramping with no cyclic hold times. This device represents the first demonstration of hold-less thermocycling within continuous-flow PCR microfluidics. This is also the first design in which continuous-flow PCR is performed within a single steady-state temperature zone. This allows for straightforward miniaturization of the channel footprint, shown in this device which has a cycle length of just 2.1 cm. With a linear thermal gradient established across the glass device, the heating and cooling ramp rates are dictated by the fluid velocity relative to the temperature gradient. Local channel orientation and cross-sectional area regulate this velocity. Thus, rapid thermocycling occurs while the PCR chip is maintained at steady state temperatures and flow rates. Glass PCR chips (25 mm×75 mm×2 mm) of both 30 and 40 serpentine cycles have been fabricated, and were used to amplify a variety of targets, including a 181-bp segment of a viral phage DNA (ΦX174) and a 108-bp segment of the Y-chromosome, amplified from human genomic DNA. With this unique combination of hold-less cycling and gradient temperature ramping, a 40-cycle PCR requires less than nine minutes, with the resulting amplicon having high yield and specificity.

Disclosed herein are methods and devices thereof that utilize a steady-state temperature gradient to create a desired fluidic thermocycling protocol within a single thermal zone. Whereas the multi-zone systems require distance and insulation to maintain the isothermal regions, the distribution of isothermal lines within the single-zone gradient system occurs spontaneously and can be easily adjusted by changing the heat flux through the substrate. In this way, the spatial distribution of the required PCR temperatures can be significantly reduced, resulting in a much smaller channel footprint, with no increase in device complexity. Additionally, by reducing two-dimensional (2-D) isothermal areas into one-dimensional (1-D) isothermal lines, residence times can be eliminated. Extensive research on the reaction kinetics of PCR has shown that residence times are not required to denature or anneal, as long as sample equilibrium is achieved. (Wittwer, 1999) Conventional PCR instrumentation has been used to demonstrate that hold-less cycling protocols can reduce amplification time, create no loss in amplification efficiency, and result in superior amplification specificity (Wittwer, 1999). In the thermal gradient system, ramp rates are the designed characteristic. Local ramp rates are dictated by the fluid velocity relative to the isothermal lines. The local velocity is determined by channel orientation and cross-sectional area. It is known that polymerase activity is the dominant rate limiting factor in PCR, with typical extension rates that can approach 100 bases per second. Thus, for short DNA targets (<200 bp) the ideal cycling protocol consists of temperature spikes to denature then anneal, followed by a moderate thermal ramp through the extension temperature. This has now been achieved with the design of the thermal gradient PCR system.

I. Experimental a. Heater Assembly

To generate the desired temperature gradient across the device, a platform was built to uniformly heat a 75 mm×25 mm PCR chip along one long edge and cool along the opposite edge, inducing a steady-state temperature gradient in the glass. By controlling the amount of heat applied to the hotter edge of the chip and the heat withdrawn from the cooler edge, the thermal gradient can be adjusted. The glass device rests on two aluminum strips, 6.35 mm wide, which extend the length of the chip. The strip corresponding to the cooler edge is coupled to a network of cooling fins. Thin-film heaters (#HR5200, Minco, MN, USA) are fixed beneath both strips—beneath the hot strip to introduce heat into the PCR chip, and beneath the cool strip to allow for the regulation of heat transfer from the chip to the cooling fins. To secure and insulate the apparatus, the components of the assembly have been fixed to a machined Teflon base. Error! Reference source not found. shows a diagram of the designed heater assembly.

b. Chip Design

"Rapid" thermal cycling has been defined as a protocol with cycle times less than 60 seconds (Wittwer, 1994). This thermal gradient PCR device has been designed to operate significantly faster than this designated limit. The desired thermocycling protocol begins with the PCR sample being brought to the denaturing temperature for several seconds, to ensure that the template DNA is fully denatured. The sample is then cooled to the annealing temperature at a rate greater than 10° C./s, after which the sample temperature immediately begins to increase steadily toward the denaturing temperature at a rate between 1° C./s and 4° C./s. At the moment when the sample reaches the denaturing temperature, it is again rapidly cooled. This "quick cool/slow heat" ramping protocol continues for at least 30 cycles, during which the desired DNA target amplifies to an appropriately high concentration. Although slow heating is only needed up to the extension temperature, for simplicity the current design heats at a constant rate.

A "hold-less" cycling protocol with varying temperature ramp rates can be achieved by establishing a thermal gradient within the glass chip such that the parallel isothermal lines run the length of the device. A serpentine microfluidic channel is imbedded in the glass. At locations along the channel where the sample should be held at a specific temperature, the channel section is located along the appropriate isothermal line. Where temperature ramping is desired, the channel passes perpendicularly across the isothermal lines. Where rapid temperature change is desired, the channels are as narrow as the fabrication process will allow, so that the sample flows quickly across the isothermal lines. Conversely, in the regions designated for slow heating, the channels are wider, which creates a slower sample velocity and thus a slower rate of temperature change. The geometry of a representative mask is shown in FIG. 1. The 30-cycle and 40-cycle chips are fabricated from 75 mm×25 mm glass blanks. The design depth for the 30-cycle chip is a uniform 50 μm. The channel widths are 110 μm and 650 μm, for the cooling and heating regions, respectively, with the passes of the channel spaced 450 μm apart. The 40-cycle chip has a channel depth of 40 μm and channel widths of 110 μm and 440 μm, with a spacing of 400 μm between the channel passes. By these design parameters, the ratio between the average cooling and heating rates is approximately 6:1 for the 30-cycle chip and 4:1 for the 40-cycle chip.

c. Chip Fabrication

The PCR chips were fabricated from soda lime glass microscope slides (#12-550A, Fisher Scientific, NH, USA) that were pre-cleaned with a piranha etch (3 $H_2SO_4$:1 $H_2O_2$) for ten minutes. A 900 nm thick film of chromium was then sputtered onto the glass blanks. Following the chromium deposition, a 2 μm thick layer of photoresist (Shipley, #1813) was spun onto the slides. The photoresist was then patterned using standard mask lithographic procedures, followed by a hard bake at 120° C. for one hour. The glass was then dipped into a chromium etchant to remove the exposed metal. With the cured photoresist and the thin chromium film serving as an etch mask for the top side of the glass, the backside of the glass was protected from the glass etchant with DuPont Kapton tape. The glass slides were then immersed in an etchant bath (1 HF:3 $HNO_3$:10 $H_2O$) until the desired etch depth was achieved (etch rate ~1.5 μm/min). After stripping off the remaining photoresist and chromium, inlet and outlet holes were drilled through the patterned glass using a diamond-tipped drill bit and drill press. The glass slides were again cleaned in a piranha etch, along with an equal number of blank slides. Each patterned and drilled slide was then fused to a blank slide by baking at 620° C. for four hours, using a protocol similar to that given by Simpson and coworkers (Simpson, 1998). Upon cooling, a Nanoport fluidic interconnect (Upchurch Scientific, WA, USA) was attached over the inlet hole of each chip.

d. Temperature Measurement

The fabricated PCR chips were affixed to the heating assembly with a small amount of thermal grease. Kapton tape was used to attach two thermocouples (Omega, CT, USA) to the top surface directly above the serpentine channel, at the location of the hottest and coolest temperatures. To examine the uniformity of the temperature gradient across the entire chip, an infrared camera (Thermacam PM390, Inframetrics Inc., MA, USA) was used to capture thermal images of the device. To remove uncertainties associated with the emissivity of the glass, chips used for the thermal imaging calibration were spray painted black (Krylon, Sherwin-Williams, OH, USA). A DC voltage was then applied to the heaters, and approximately 10 minutes was allowed for the system to equilibrate. Once the thermal gradient stabilized, measurements from the thermocouples and the IR camera were recorded and compared. Once the temperature of the chip surface was known, the temperature of the microchannel ($T_c$) within the glass was obtained from the following equation:

$$T_c = \left(\frac{Lh}{k} + 1\right) \cdot (T_s - T_\infty) + T_\infty \tag{1}$$

where L is the distance from the chip surface to the imbedded channel, h is the average convective heat transfer coefficient at the surface/air interface, k is the thermal conductivity of the glass, $T_s$ is the temperature of the surface, and $T_\infty$ is the ambient temperature. Although it is understood that some temperature lag will develop between the moving fluid and the glass walls of the channel, for the intended temperatures and flow rates the fluid temperature is approximately the same temperature as the surrounding glass. In this way, the temperature of the sample at every position can be inferred from the thermometry data obtained from the surface of the chip.

There is also a lateral temperature distribution within the microchannel due to heat transfer through the flowing fluid. With a linear temperature gradient across the substrate, a constant heat rate exists in the channel sections that run in the direction of the gradient. The fully developed temperature profile under this condition can be found analytically for basic channel geometries (Kays, 1993). For a circular channel, the lateral temperature distribution (T) is given as:

$$T = T_c - \frac{2V}{\alpha}\frac{dT_m}{dx}\left(\frac{3r_0^2}{16} + \frac{r^4}{16r_0^2} - \frac{r^2}{4}\right) \quad (2)$$

where $T_c$ is the temperature at the channel wall, V is the average fluid velocity, $\alpha$ is the molecular thermal diffusivity, $dT_m/dx$ is the temperature gradient along the channel wall (in the direction of fluid flow), $r_0$ is the radius of the channel, and r is the distance from the centerline at which the fluid temperature (T) is calculated.

e. PCR Experiments

To demonstrate the capability of the thermal gradient PCR chip, small targets were amplified from both viral DNA and human genomic DNA. As part of these tests, a 110-bp and 181-bp segment of a viral phage DNA template ($\Phi$X174, $10^5$ copies/$\mu$l) were amplified on a 30-cycle chip, and a 108-bp segment of the Y-chromosome was amplified from human genomic DNA (5 ng/$\mu$l) on the 40-cycle chip. In addition to the template DNA, the PCR mixture used for amplification consisted of 0.5 $\mu$M of each primer [the primer sequences for the selected targets are as follows: $\Phi$X174, 110-bp (F-GGT-TCGTCAAGGACTGGTTT, SEQ ID NO: 1, R-TTGAA-CAGCATCGGACTCAG, SEQ ID NO: 2; $\Phi$X174, 181-bp (F-GCTTCCATGACGCAGAAGTT, SEQ ID NO: 3, R-GC-GAAAGGTCGCAAAGTAAG, SEQ ID NO: 4) Y-chromosome, 108-bp (F-ATTACACTACATTCCCTTCCA, SEQ ID NO: 5, R-AGTGAAATTGTATGCAGTAGA, SEQ ID NO: 6)], 200 mM of each deoxynucleotide triphosphate (dNTP), 0.4 U of KlenTaq1 polymerase (AB Peptides, MO, USA), 88 ng of TaqStart antibody (ClonTech, CA, USA), 3 mM $MgCl_2$, and 1X LCGreen Plus (Idaho Technology, UT, USA) in 50 mM Tris (pH 8.3) and 250 ng/ml bovine serum albumin (BSA). To compare amplification characteristics (speed, specificity, and yield), portions of each PCR mixture were amplified in both the thermal gradient PCR chip and commercial PCR equipment (LightCycler®, Roche, IN, USA). To validate the amplification, negative controls (without template DNA) were also amplified to ascertain whether the resulting amplicon is a product of residual contamination.

Since the chips were to be used for a substantial number of amplification experiments, a cleaning protocol was developed to effectively remove the residual DNA from the microchannel. The protocol consists of a 100 $\mu$l purification wash of 15% Clorox bleach and 2% detergent (7X-O-Matic, ICN Biomedicals, OH, USA), followed by two 100 $\mu$l plugs of deionized water separated by a 50 $\mu$l plug of mineral oil. The cleaning/rinsing reagents were passed through the chip at a flow rate of approximately 30 $\mu$l/min. With the PCR chip in the heating assembly and the thermal gradient established, PCR was performed by loading the PCR mixture into a syringe (#1705, Hamilton, Nev., USA) and pumped (#KDS120, KD Scientific, MA, USA) continuously through the chip at a steady rate. The PCR sample containing the viral template was pumped through the 30-cycle chip at a rate of 1.5 $\mu$l/min. The sample containing the human genomic template was pumped through the 40-cycle device at a rate of 2 $\mu$l/min. After filling the channel, sample began to collect at the outlet hole, from which it was collected in 5 $\mu$l increments for analysis. After the desired amount of sample was passed through the channel, the system was cleaned as explained. Serial experiments were performed to determine any cross-contamination between samples. For serial experiments, the thermal gradient was left unchanged while the pumping, removal, and cleaning protocols were repeated for each successive sample. Positive and negative controls from both the thermal gradient PCR chip and the LightCycler were analyzed on a stained 1.5% agarose gel.

II. Results and Discussion

FIG. 3 shows photographs of the completed device, which measures approximately 8 cm×10 cm×2 cm. External interfaces to the system include the electrical leads for the thin-film heaters and the Nanoport fitting (in the figure, bottom left corner of the chip) where the PCR samples are introduced. During fabrication of the glass channel, etched features were measured with a stylus profilometer (P-10, KLA-Tencor, CA, USA). Dimensions were found to be within 5% of the design specifications. As assembled, the channel is not directly above the aluminum strips. Rather, it is located between the strips, where the temperature gradient is linear and where the entire channel is optically accessible from above and below.

a. Temperature Calibration

Equation 1 was used to approximate the channel temperature from the measured surface temperature. The approximate distance between the glass surface and the microchannel (L) is 0.95 mm; the thermal conductivity (k) of borosilicate glass is 1.1 W/m-K; the average heat transfer coefficient (h) is approximately 5 W/m²-K for the temperatures to which the device will be subject. Using these values and an ambient temperature of 22° C., the difference between the surface temperature and the channel temperature is less than 0.4° C.

The approximate lateral temperature distribution within the microchannel has been calculated using Equation 2. Assuming a molecular thermal diffusivity of $164\times10^{-9}$ m²/s (water @ 80° C.), a hydraulic diameter of 100 $\mu$m, an average fluid velocity of 10 mm/s, and an axial temperature gradient of 4 deg/mm, the change in temperature within the channel is on the order of 0.25° C. This temperature lag, making the fluid in center of the channel cooler during heating and warmer during cooling, can be considered to have a negligible effect on the PCR efficiency.

With the device fully assembled, voltage was applied to the heaters. After 10 minutes, equilibrium was established such that the microfluidic channel was within a stable temperature distribution bounded by 95° C. and 60° C. (+/−1° C.). The surface temperature was measured at two locations with the thermocouples, and then the entire surface was imaged with the infrared camera.

FIG. 3 shows a typical image recorded by the IR camera, as well as a pseudo-3D image of the same data, which allows for better visualization of the temperature gradient across the chip. The glass in the region of the microfluidic channel experiences an average temperature gradient of 3.5° C./mm, as shown in FIG. 4. Above approximately 78° C. the gradient is higher than the average, reaching a maximum value of 4.5° C./mm at the denaturing temperature. Below 78° C. the gradient slightly decreases, with a 2.5° C./mm minimum at the annealing temperature. The curvature of the gradient results from the convection of heat away from the surface of the glass. Were the chip completely insulated the heat transfer would be strictly one-dimensional and the temperature distribution would be perfectly linear. However, this variation in the gradient is a favorable one for PCR, since the critical ramping time is between the annealing and extension temperatures. Therefore, insulating the surface is unnecessary.

b. Stochastic Variation in Individual DNA Velocities

During proper amplification conditions, there are only two sizes of DNA in the microfluidic channel: the template DNA of very large size (kbp, Mbp, or more), and the amplicon, which commonly does not exceed 200 bp in length. The 1-dimensional molecular diffusion coefficient for the shorter strands is on the order of 200 $\mu m^2/s$ (Lapham, 1997) (Pappaert, 2005). This mobility corresponds to random Brownian displacement on the order of 25 μm every 1.5 seconds. With a channel depth of 50 μm and an average heating time of 15 seconds, it is likely that each DNA molecule spends significant time in all velocity streamlines. Thus, the average value of the fluid velocity can likewise be assumed for all small DNA fragments. For very large DNA (>100 kbp), hydrodynamic effects dominate, and the DNA is drawn into the faster flow regions toward the center of the channel, being found to always migrate with a size-dependent velocity between the average and the maximum fluid velocity (Jendrejack, 2003). For these reasons, variations in individual velocities for both the template DNA and the generated amplicon can be ignored, and average values can be assumed. While self-diffusion rates for the other PCR constituents may vary, individual dwell times for these molecules are irrelevant.

c. PCR Results

Figure 5:
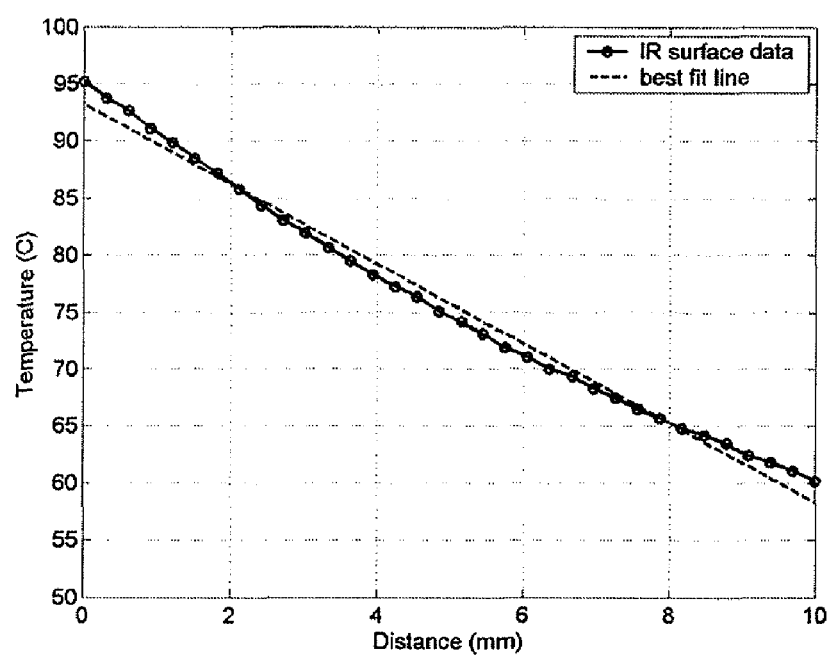
FIG. 5 shows the fluorescent image of PCR products separated in a 1.5% agarose gel after a 30-cycle amplification. The target is a 181-bp segment of the ΦX174 phage DNA. Samples from the LightCycler were amplified in 10 minutes and positive and negative controls are shown in lanes 2 and 3, respectively. Lanes 4-8 show consecutive samples amplified in the thermal gradient PCR chip (11 minutes per sample), the last of which was a negative control. The slightly brighter signal from the chip-amplified product is due to partial evaporation of the sample. Faint bands associated with primer dimers are visible.
Figure 7:
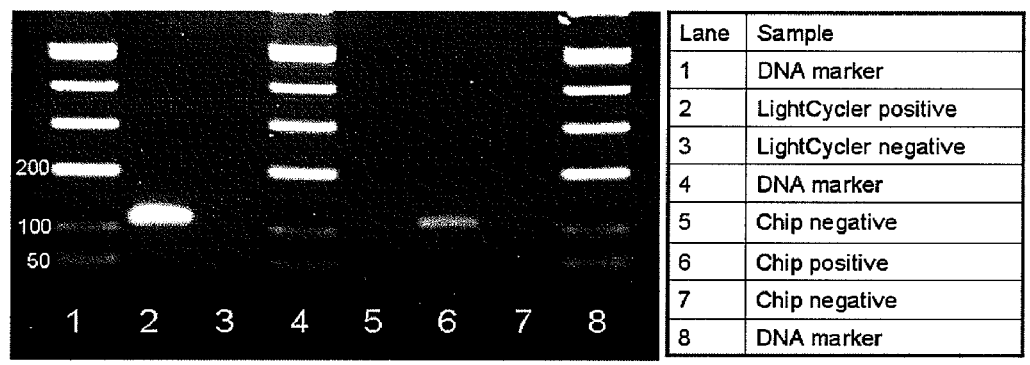
FIG. 7 shows samples containing primer sets corresponding to the 108-bp product were amplified from human genomic DNA with a 40-cycle PCR. Samples amplified on the LightCycler (13 minutes) and on the thermal gradient PCR chip (8.5 minutes) are shown. The negative controls (lane 5, 7) passed through the device before and after the positive amplification (lane 6) to confirm that the amplification is from genomic template.

The control samples were amplified on the LightCycler in 10 minutes for the 30-cycle PCR and 13 minutes for the 40-cycle PCR. By pumping sample through the 30-cycle thermal gradient chip at 1.5 μl/min, sample started to accumulate at the outlet hole after 11 minutes, averaging 22 seconds per amplification cycle. Within each cycle, the sample was cooled from 95° C. to 60° C. in approximately 3 seconds or an average cooling rate of nearly 12° C./s. The heating occurred over 18 seconds, at a rate of approximately 2° C./s. For the 40-cycle PCR chip pumped at 2 μl/min, the sample began to exit after 8.5 minutes, 35% faster than the LightCycler. The average cycle time for this PCR was less than 13 seconds, with average cooling and heating rates of 14° C./s and 3° C./s, respectively. Both chip designs were used for multiple amplifications by repeating the pump/remove/clean protocol, after which representative sample volumes were analyzed on electrophoresis gels. Consecutive amplifications of identical PCR samples, as shown in FIG. 5, indicate the repeatability of the thermal gradient device. By amplifying different targets in serial fashion, the absence of cross-contamination between samples is demonstrated. Amplifying negative samples before and after a positive sample, as shown in FIG. 7, confirms that the amplicon was copied from the intended template. The cleaning protocol was able to adequately remove the PCR residue between amplifications, allowing for extended use with biological samples.

A precise way to determine the efficiency of a PCR device is to compare the real-time amplification of serially diluted template of known concentration. The thermal gradient PCR chip is not currently compatible with real-time detection. Estimates of efficiency and specificity were therefore made by visual comparison of gel electrophoregrams of sample amplified on the microchip and the control system. Since the chip-amplified product is generally as concentrated and as clean as that of the LightCycler, comparable amplification efficiency and specificity can be assumed.

When the 40-cycle thermal gradient chip was cycled 35% faster than the LightCycler, lower yield was consistently obtained. Lower yields with faster cycle times are a common finding in the CF-PCR literature (Hashimoto, 2004; Kopp, 1998; Schneegass, 2001). While no attempt was made to amplify DNA targets above 200 by in length, it should be noted that the great majority of genetic testing and pathogen detection involve target sequences less than 200-bp in size. For this reason, the initial testing of the device focused on the lower range of target sizes. While it is probable that the gradient system will have a low limit on the size of amplifiable target, such applications are not common enough to be considered a noteworthy disadvantage of the system.

d. Microchip PCR

While high through-put is the desired characteristic for applications such as drug discovery, and genetic scanning/mapping, it is fast turn-around time for single-or several-sample analyses that allows for the development of integrated palm-top or bench-top medical instruments. When trained professionals are provided such tools for rapid pathogen-detection or disease genotyping, the accuracy and timeliness of medical diagnosis and treatment improves.

A single experiment can be performed in approximately one hour. In addition to the amplification time, this includes 10 minutes for the instrument to warm up, 5 minutes to prepare the PCR sample from pre-extracted DNA and other prepared reagents, 5 minutes for sample loading, 5 minutes for the extraction of each of the several 5 μl aliquots, and 15 minutes to clean the chip between samples and allow for the temperature gradient to re-stabilize. The overall time of experiment can potentially be halved by reducing the number of aliquots collected, and preparing multiple samples in advance. Although the thermal gradient PCR device operates with a reduced amplification time, all other periphery processes (DNA extraction, sample mixing, post-processing) follow traditional laboratory-based protocols. Thus, the total time of experiment is not significantly reduced. Significant, competitive reduction in overall time will only come through full integration of all preparatory and analytical steps (Easley, 2006).

Figure 8:
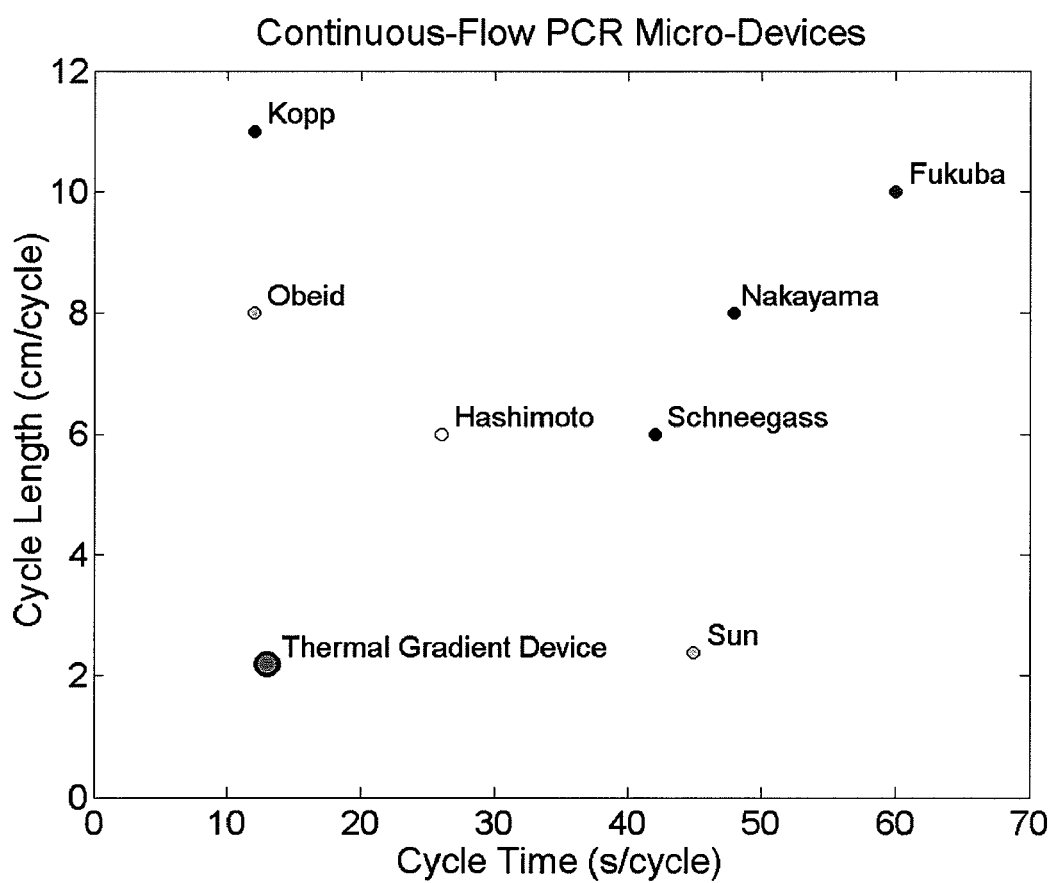
FIG. 8 shows a graphical summary of the several CF-PCR designs, indicating the reported cycle time and cycle length for each device. Shorter cycle time implies faster amplification, and shorter cycle length results in a smaller device footprint. Previous designs are labeled as found in Crews (2007). The device presented is labeled "Thermal Gradient Device".

Two primary metrics for micro-PCR are the speed of the amplification and the size of the device. FIG. 8 Figure graphs these two characteristics for the current design as well as for previous CF-PCR devices. While some previous CF-PCR devices have been operated with similarly rapid cycle times, and some have approached the small footprint of the thermal gradient device, only through this present technique have both high speed and small size been achieved together. This can be attributed to the single-zone temperature profile of the device, allowing for short cycle length with no residence times, and the reasonably high width ratios that produce the required slow heating rate with fast cooling.

The unique spatial spreading of the different PCR stages in this thermal gradient device introduces the opportunity for identifying the amplified product during the PCR, thus totally eliminating the need for additional time or sample transport for successive testing. Since each location along the channel possesses a unique cycle/temperature identity, fluorescence imaging techniques can be used to characterize both the amplification behavior and the unique dsDNA melting signature of the amplicon (Ririe, 1997) from a single fluorescence photograph of the device (Mao, 2002). Such an approach also eliminates the oft-cited disadvantage of cycle number flexibility commonly associated with CF-PCR systems (Obeid, 2003b), since the product analysis can be performed for all cycles at once. This proposed integration with fluorescence analysis is possible with precise mapping of the temperature distribution and the clear optical access to the entire channel that is achieved with thermal gradient PCR.

III. Conclusion

This new continuous-flow thermal gradient PCR technique is capable of rapidly amplifying DNA targets from both viral and human genomic DNA. A microfluidic thermocycling protocol was instituted with no hold times and ramp rates based on reaction kinetics. This was achieved by inducing a quasi-linear temperature gradient in a glass microfluidic chip containing a uniquely designed serpentine channel. Cycle times of 13 seconds are sufficient to amplify targets from human genomic DNA. A cleaning protocol was developed to allow serial amplification of different PCR samples on the same chip without cross-contamination between the samples.

Example 2

Product Differentiation During Continuous-Flow Thermal Gradient PCR

I. Experimental
  a. Thermal Gradient PCR Device
Device Fabrication

The 25 mm×75 mm×2 mm microfluidic chip was fabricated from soda lime glass. To create the imbedded channel, a glass blank was patterned using ultraviolet (UV) photolithography and an etchant solution of hydrofluoric (HF) and nitric acid ($HNO_3$), then fusion bonded to a second glass blank. The full fabrication protocol has been previously reported (Crews 2007). The final channel contained serpentine passes having alternating widths of 110 µm and 650 µm, and a uniform depth of 50 µm. The passes were placed 450 µm apart. The channel geometry allowed for the completion of 30 thermal amplification cycles in a total channel length of less than 80 cm, and a volume of approximately 6 µl.

The thermal gradient was established in the substrate by placing the device in a heating/cooling apparatus previously discussed. Uniform thermal contact was made with the long edges of the PCR chip by using thermal interface pads (TP-1500-T0.25, Dow Corning, MI, USA) with a thermally conductive adhesive coating. A steady-state temperature gradient was established by applying voltage to the heating apparatus such that heat would flow through the chip to the cooling fins. A final power of 6.0 W (5.56 V, 1.08 A) and 1.18 W (2.50 V, 0.47 A) was applied to the thin film heaters (#HR5200, Minco, MN, USA) placed beneath the heating and cooling edges of the chip, respectively, to generate a gradient from 60° C. to 95° C. across the 1 cm length of each channel pass. For fast thermal equilibration, equal voltages of 10 V were applied for 60 seconds, followed by 8 V and 4 V (for the heating and cooling sides, respectively) for 60 seconds, after which the final voltages were set for the duration of the experiment. Thermocouples affixed to glass were used to monitor the range of temperatures, and infrared (IR) thermometry was used to characterize the linearity of the thermal gradient (Crews 2007).

b. PCR Protocol

The same recipe was used for all PCR samples with the exception of the target-specific primer sequence. A 108-bp section of the DYZ1 gene (Handyside 1990) was amplified, as well as two loci within Cytochrome P-450 2C9 (Hill 2006), encompassing exon 3 and exon 7 (denoted here as CYP2 and CYP3, respectively) (The primer sequences for the selected targets are as follows:
  DYZ1, 108-bp [F-ATTACACTACATTCCCTTCCA (SEQ ID NO: 5),
    R-AGTGAAATTGTATGCAGTAGA, (SEQ ID NO: 6);
  CYP2, 122-bp F-GAATTTTGGGATGGGGAAGAG (SEQ ID NO: 7),
    R-TCCAGTAAGGTCAGTGATATGG (SEQ ID NO: 8);
  CYP3, 134-bp (F-CATGCAAGACAGGAGCCA (SEQ ID NO: 9),
    R-TGGGAATGAGATAGTTTCTGAATTTA, (SEQ ID NO: 10)]. The PCR mixtures contained 5 ng/µl of human genomic DNA, 0.5 µM of each primer, 200 mM of each deoxynucleotide triphosphate (dNTP), 0.4 U of KlenTaq1 polymerase (AB Peptides, MO, USA), 6.4 ng of Anti-Taq Monoclonal Antibody (eENZYME LLC, Gaithersburg, Md., USA), 3 mM $MgCl_2$, 1X LCGreen Plus (Idaho Technology, UT, USA), and 250 ng/ml bovine serum albumin (BSA) in a 50 mM Tris (pH 8.3) buffer. The cleaning mixture used between amplification tests contained 15% Clorox bleach and 2% detergent (7X-O-Matic, ICN Biomedicals, OH, USA). The specific cleaning protocol has been given previously (Crews 2007).

For these experiments, a 90 µl mixture volume was prepared, from which 10 µl were removed for amplification on a control system (LightCycler®, Roche, IN, USA). As suggested by Nakayama and co-workers (2006), a small plug of mineral oil (~8 µl) was first introduced into the chip to reduce bubble formation in the sample, after which the PCR mixture was pumped through the channel at a rate of 1.5 µl/min. After 10 minutes, when the sample began exiting the chip, the elution was removed in 5 µl aliquots. Five or six aliquots were obtained for each PCR sample, after which the remaining PCR mixture in the chip, syringe, and tubing were discarded, and the chip cleaned prior injection of a subsequent sample. The serial elutions were analyzed with the control samples on a DNA melting analysis instrument (HR-1, Idaho Technology, UT, USA). Select elutions were also injected into a 1.5% agarose gel for electrophoretic size separation.

c. Fluorescence Acquisition

Figure 9:
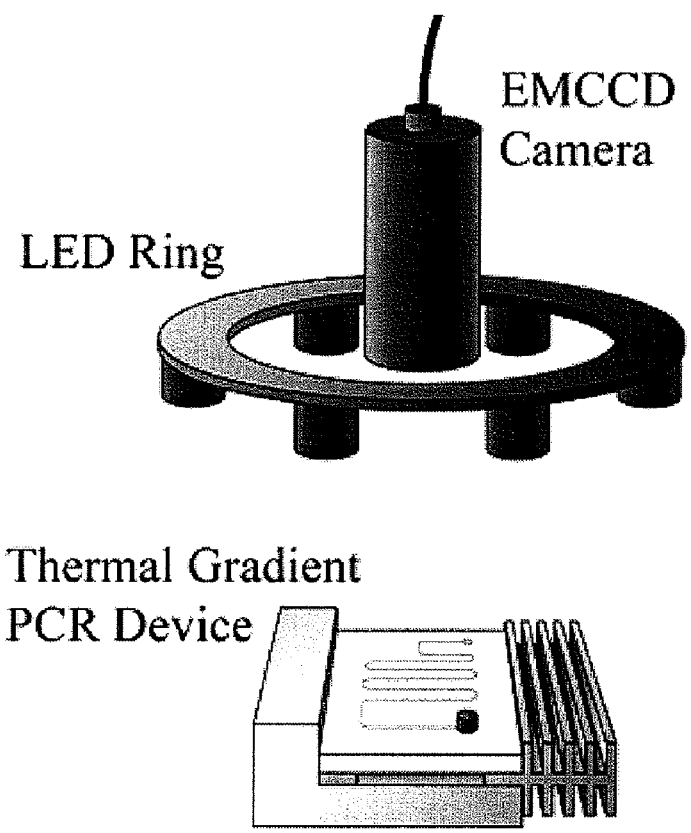
FIG. 9 shows the fluorescence acquisition system consists of a band-pass filtered (450/50 nm) LED ring, and an Andor iXon EMCCD camera, equipped with a 60 mm lens with a long-pass filter (485 nm). By placing the thermal gradient PCR device beneath this optical system, the dye in the solution is uniformly excited and much of the microfluidic channel can be imaged at one time.

To excite the dye in the PCR mixture, the thermal gradient microfluidic device was placed beneath a ring of LEDs. Since the LC Green Plus dye has an optimum excitation wavelength between 440 nm and 470 nm and emits between 470 nm and 520 nm, the LEDs (Luxeon LXH2-BR02, Philips, CA, USA), which emit at a peak wavelength of 455 nm, were band-gap filtered to 450/50 nm (HQ450/50X, Chroma Technology Corp, VT, USA). The fluorescence from the PCR sample was detected by an Andor iXon EMCCD camera (DV885JCS-VP, Andor Technology, Belfast, Northern Ireland), positioned above the thermal gradient micro-device. The camera was fitted with an optical lens (EF-S 60 mm f/2.8 Macro USM, Canon Inc., Tokyo, Japan) with a 485 nm long-pass filter (HQ485LP, Chroma Technology Corp, VT, USA). FIG. 9 shows a schematic of the thermal gradient PCR device beneath the LED ring and camera. An exposure time of 5 seconds was used to image the microfluidic channel. To detect only the change in fluorescence of the microchannel, a background image was taken which was automatically subtracted from the later images. The background was acquired with the LEDs illuminating the device while the mineral oil filled the channel. Beginning when the mineral oil passed out of the chip, the device was imaged after each 5 µl sample was removed.

d. Spatial Melt Analysis

The acquired fluorescence images were analyzed using a GUI (graphical user interface) that was developed in MATLAB for this application. The program allows the user to designate the location and value of the high and low temperatures that bound the microchannel, as well as the direction of heat flow across the chip. A rectangle is then drawn to designate the region to be analyzed. The brightness of the selected pixels is then averaged laterally, such that the resolution in the axial (channel-wise) direction is not reduced. The program then couples the spatial distribution of the fluorescence with the temperature distribution across the channel, using the two previously input temperatures and an assumed linear thermal gradient between them. The program then exports the calculated temperature and fluorescence data to a LabVIEW™ program (Melting Wizard, v.3.0) that compares spatial (from the thermal gradient devices) and/or time-dependent (from the HR-1) melting curves of multiple samples. The Melting Wizard algorithm is summarized as follows: The temperature range is covered by overlapping intervals of fixed width. In each interval, the software performs a nonlinear least-squares fit of the raw fluorescence data points, F(T) by an exponential curve:

$$\exp(T)=Ce^{aT} \tag{1}$$

The dependence of the decay factor, a(T), calculated in this manner upon the mean temperature, T, of the fit points in each interval, behaves much like a derivative melting curve. In contrast to the raw derivative curve F'(T), a(T) is constant in temperature regions without significant target DNA melting, where fluorescence due to other interactions decays exponentially. The software numerically integrates a(T) to obtain the melting curve M(T), a step that inherently smoothes high-frequency noise. Upon normalization, this filtered version of the raw data allows for a cross-platform comparison of DNA melting experiments, reducing the dependence on specific instrument characteristics.

II. Results and Discussion a. PCR Experiments

Figure 10:
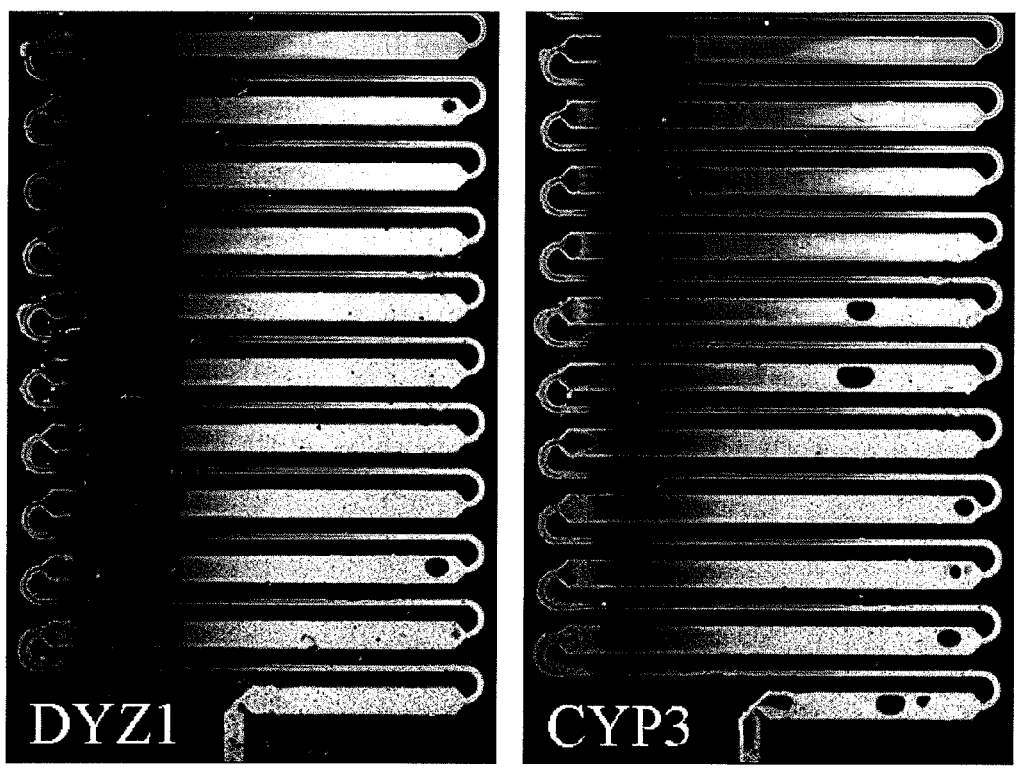
FIG. 10 shows fluorescent images of the channel during thermal gradient PCR of two different targets. The random dark ellipsoids within the channel are slow-moving bubbles. These photos show cycles 20 through 30 of the 30-cycle device. As the cycle number increases (top to bottom in the photo), the flowing sample continues to amplify. The denaturing of the amplicon with increasing temperature (right to left in this photo) can be seen as a vertical line where the fluorescent signal is quenched. The image of the DYZ1 sample shows this melt line extending through all visible cycles, indicating that this sample already has a strong amplicon concentration after 20 cycles. The melt line for the CYP3 sample, on the other hand, begins to be visible after 26 amplification cycles, indicating the point at which the amplicon concentration is measurable on this system.

Fluorescent images were taken of the thermal gradient device every five minutes, beginning when the channel was completely filled with the PCR solution. The first photograph revealed no fluorescence from the cycles within the camera's field of view. The following photograph, taken after the first 5 μl was eluted from the chip, showed a little fluorescence at the early cycles, but still no fluorescence at the final cycles. The fluorescent signal continued to increase down the channel, but at a rate significantly slower than that of fluid flow. After the third sample was removed from the chip, fluorescence was observed at all cycles. This final fluorescence distribution could be considered steady-state, since it remained virtually unchanged for the remainder of the photographs. Typical images of the device at this point, showing the final 10 cycles of a 30-cycle amplification cycles 20-30, are shown in FIG. 10. Within these higher-numbered cycles, the fluorescence can be seen to gradually decrease with increasing temperature, until the signal is suddenly quenched when the sample reaches the temperature of denaturation. By viewing this phenomenon over multiple cycles, a vertical line appears which indicates the melting temperature of the amplified product. This vertical melting line is only visible when an adequate amount of amplicon is present in the channel. By observing the melt line from the two photographs in FIG. 10, it can be seen that the DYZ1 sample amplified much earlier than the CYP3 sample. Such is typical of these two samples, as can be seen from real-time PCR data obtained from the LightCycler. When amplified on the commercial platform, the DYZ1 sample begins to show measurable amplification after 13 cycles, while fluorescence from the CYP3 sample begins to increase after 21 cycles.

Figure 11:
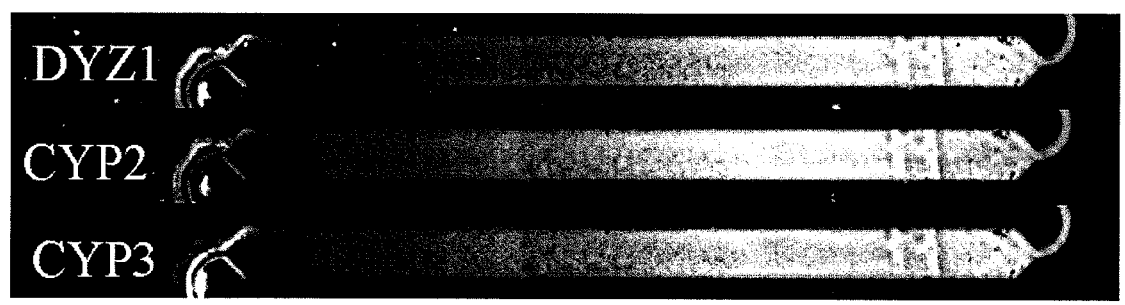
FIG. 11 shows a comparison of the spatial melts of three samples amplified from genomic DNA. For each sample, the denaturing of the ds-DNA into ss-DNA can be observed by the extinguishing of the fluorescent signal. The differences between the melting behavior of each sample can be observed. The bright stains seen to the left of each melt seem to be cause by interactions between the BSA and the fluorescent dye at high temperature.

Photos such as that shown in FIG. 10 were obtained for the three DNA targets, with observable differences in the melting behavior of each sample. The final cycles of each PCR are shown together in FIG. 11. The aforementioned GUI was used to extract melting curves of each sample from the photographs. The melting temperature of the DYZ1 sample is several degrees lower than that of the other two. The CYP2 and CYP3 samples can be distinguished by the shape of their melting curve as well as a slight shift between temperatures where full denaturing occurs. The CYP3 target has regions of its sequence that denature several degrees below the rest, resulting in an early "sagging" of the melt curve. The observable presence of two melting regimes is a specific characteristic of the nucleotide pattern of the CYP3 sample, and is commonly found among DNA melting studies (Sundberg 2007). Although the melt curves in this figure are identifiable, irregularities in the fluorescence can be seen. The presence of these undesirable artefacts is attributed to random surface roughness on the surface of the glass device and possible nucleation of BSA/dye semi-solids. The roughening of the glass surface occurs during the fusion bonding process, and causes irregular refraction of the fluorescent signal during device operation. The suspected precipitation of the BSA is likely caused by its non-optimum concentration in the PCR recipe, as well as surface interactions resulting from the high surface-to-volume ratio common in microfluidics. Solutions to these two issues will potentially allow for greater shape resolution of the melting curves, and are currently under investigation.

When the five aliquots were eluted from the device, they were melting on the HR-1 to determine the success of the amplification. Identical PCR mixtures amplified on the Light-Cycler were used as control samples. While the first elution shows no amplification, the successive volumes increase in DNA concentration until the corresponding melt curves become comparable to those from the LightCycler samples. Control sample amplifications were also melted for comparison. As was observed in the spatial melt curves, the DYZ1 samples melts at a lower temperature than the other two samples, and the CYP3 melt curve has two regimes, resulting in an early dip in the curve, while the melt curve of the CYP2 sample only shows one. The similarities between the shape of the melting curves from samples amplified on the LightCycler and the thermal gradient PCR device indicate the amplicon match between the two PCR platforms. The height of each melt curve, particularly in the region where the DNA denatures, is an indicator of relative fluorescence intensity, and thus DNA concentration. Since the melt curves for the chip-amplified sample have approximately the same magnitude as those from the LightCycler, it can be concluded that the thermal gradient PCR chip and the LightCycler posses a similar amplification efficiency.

Figure 12:
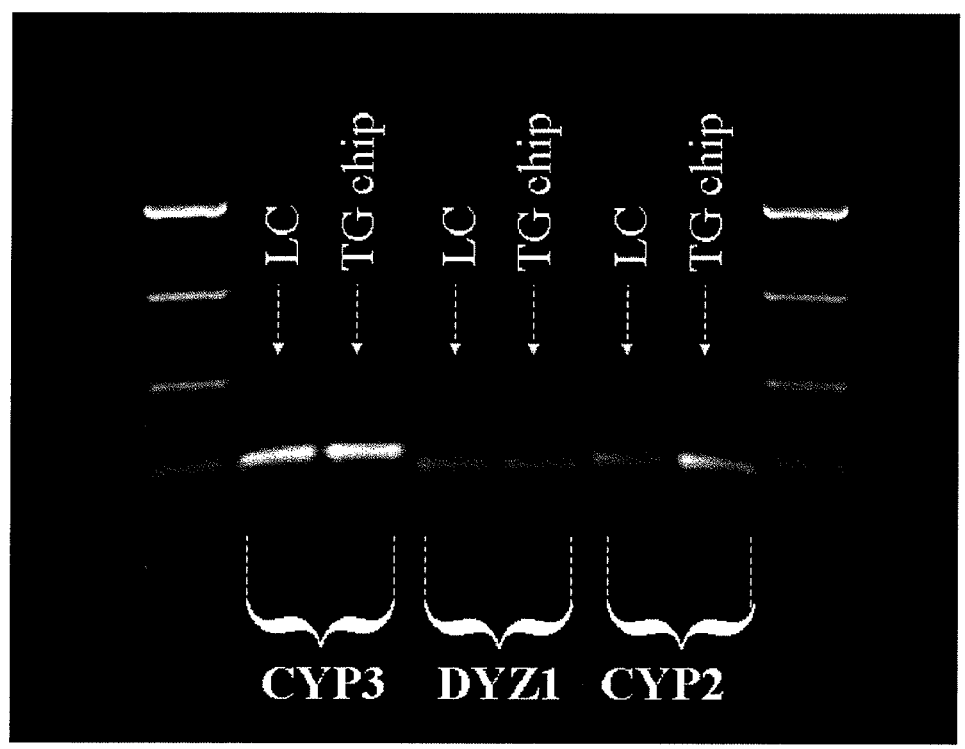
FIG. 12 shows a gel electrophoregram comparing the size, concentration, and specificity of the LightCycler ("LC") and the thermal gradient PCR device ("TG chip") for the amplifications of the CYP3 (134-mer), the DYZ1 (108-mer), and the CYP2 (122-mer) targets from human genomic DNA.

Gel electrophoresis was also used to demonstrate the comparable specificity and concentration of the chip-amplified and control samples. Samples amplified on the LightCycler were run beside samples of the same target, amplified on the thermal gradient microdevice. The electrophoregram showing this comparison is shown in FIG. 12. The horizontal agreement between bands and their relative brightness verify that the sizes and concentrations of amplicon generated by the two platforms are nearly identical. Examining the CYP2 samples shown in this gel, two fainter bands can be seen above the bright primary band. This indicates the unexpected amplification of two additional regions of the DNA. They are above the primary band, indicating larger size than the 122-bp CYP2 target. Because the fluorescence from those additional bands is much fainter even though the fragments are larger, it can be concluded that their amplification was secondary in preference to that of the targeted sequence. It should be noted that these minor bands were slightly amplified by both systems, which demonstrates the similarities in specificity of the two PCR platforms.

b. Device Concept

The spatial geometry of the thermal gradient device produces a channel footprint substantially larger than single-well stationary PCR systems (Northrup 1998). Therefore, no attempt is being made to perform massively parallel PCR with this thermal gradient system. The operation of this current system is capable of rapid single sample testing. This system, when fully integrated with DNA extraction (Cao 2006) and sample preparation (Garstecki 2006) microfluidics, can be used for the individual genotyping or pathogen detection of one patient at a time. Reasonable multiplexing of multiple microfluidic chips can be done to simultaneously analyze a small number of DNA samples or genes, and heating platforms compatible with such operation are currently being considered.

There are two features of the thermal gradient device that allow for the fluorescent signal from the entire PCR to be acquired with a single photograph. First, as is characteristic of all CF-PCR devices, the amplification is spread spatially, where each pixel of the channel image corresponds to a certain temperature and cycle number. While plug flow (small sample volumes that span only a small portion of the microfluidic channel) would require serial photographs to observe amplification behavior over multiple PCR cycles, a continuous flow of PCR mixture contains sample at all cycles and temperatures simultaneously. The second vital feature of the device is the uniformity of the thermal ramping of the sample, which is unique to the thermal gradient PCR microchip. Without exception, previous CF-PCR designs place steady-state heat sources beneath the several regions of the microchannel in order to create isothermal zones separated by very sharp temperature transitions. With device design and experimental emphasis on the several distinct PCR temperatures (e.g. annealing—60°, extension—72°, denaturing—95°), the transitional temperature range over which the DNA melting actually occurs is not considered. Were those devices to be examined closely, it would likely be found that the "step function" temperature distribution across the substrate introduces such a level of thermal uncertainty within the transitional denaturing range that accurate correlation between the spatial temperature and fluorescence distributions could not be achieved. In comparison, the thermal gradient PCR device maintains a well-defined, nearly uniform temperature distribution throughout the microchannel. With a gradient of approximately 3.5° C./mm, the field of view used in these experiments give the camera a resolution better than 0.1° C./pixel, which is on the same order of magnitude as the thermal variations within the channel due to convective heat transfer (Crews 2007). As has been demonstrated here, this resolution is sufficient to capture the melting signature of the amplifying DNA. By expanding the camera's field of view to include more amplification cycles, cycle-dependent amplification data can be acquired that would allow for the calculation of initial template concentration (Belgrader 2003) in addition to the amplicon identification that has been demonstrated. A camera with a greater pixel density can be used to obtain improved spatial fluorescence resolution.

III. Conclusion

The results obtained from this work have shown that the spatial melting analysis of DNA during CF-PCR can be achieved. By using the thermal gradient PCR system to induce steady temperature ramping in the flowing sample, a single photograph of the fluorescence distribution across the channel can provide this sample identification. This gives the ability to analyze the DNA after arbitrary or multiple amplification cycles without disrupting the PCR. While this technique requires a significant increase in auxiliary instrumentation, the PCR now becomes the final step in the analytical process. This has been demonstrated by comparing the amplification of three targets amplified from human genomic DNA. This system can allow for greater precision in the melting curve acquisition, even allowing for the detection of single nucleotide polymorphisms (SNPs) in the amplifying samples. This results in a powerful tool for rapid individual DNA testing.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

Example 3

Thermal Gradient PCR in a Continuous-Flow Microchip

A new continuous-flow PCR microchip has been developed that operates by cycling a prepared sample within a spatial temperature gradient. This design allows for minimal thermal residence times—a key feature of the protocols used by the fastest commercial PCR equipment. Since thermal gradients are a natural effect of heat dissipation, the appropriate temperature distribution for PCR can be generated by a minimum of one heater held at a steady state temperature. With a thermal gradient of more than 3° C./mm across the width of the chip, each complete PCR cycle requires approximately 2 cm of channel length. These glass chips were manufactured using standard glass microfabrication methods as well as the Xurographic rapid prototyping technique. Targets of 110 bp and 181 bp were amplified from $\Phi$X174 plasmid DNA on these thermal gradient chips as well as on commercial PCR equipment, then subsequently analyzed by gel electrophoresis. Visual inspection of fluorescent images of the stained gels shows that the amplicon size and yield for the systems are comparable.

Since common PCR protocols can require many tens of amplification cycles, the temperature cycling time is very important. In traditional PCR, the surface-to-volume ratio of the sample is relatively low, which impedes the heat transfer between the sample and the sample container. This increases the time needed to reach thermal equilibrium. This, among other factors, has led to the establishment of an "Equilibrium Paradigm", in which it was understood that the PCR mixture should be heated to each of the three temperatures and held for a specific length of time. Such a procedure is necessary to allow large volumes to reach thermal equilibrium sufficient for the corresponding reactions to occur. However, both denaturation and annealing occur very quickly (<1 sec) once the entire sample has reached the required temperatures, and typical extension rates are on the order of 100 bases per second, under ideal conditions. In addition, when relatively small DNA targets are being amplified, full extension can occur during the transition between temperatures, and no hold time is required. Such understanding has led to the development of the "Kinetic Paradigm", which allows for faster amplification cycles, no loss in amplification efficiency, and superior amplification selectivity.

Figure 15:
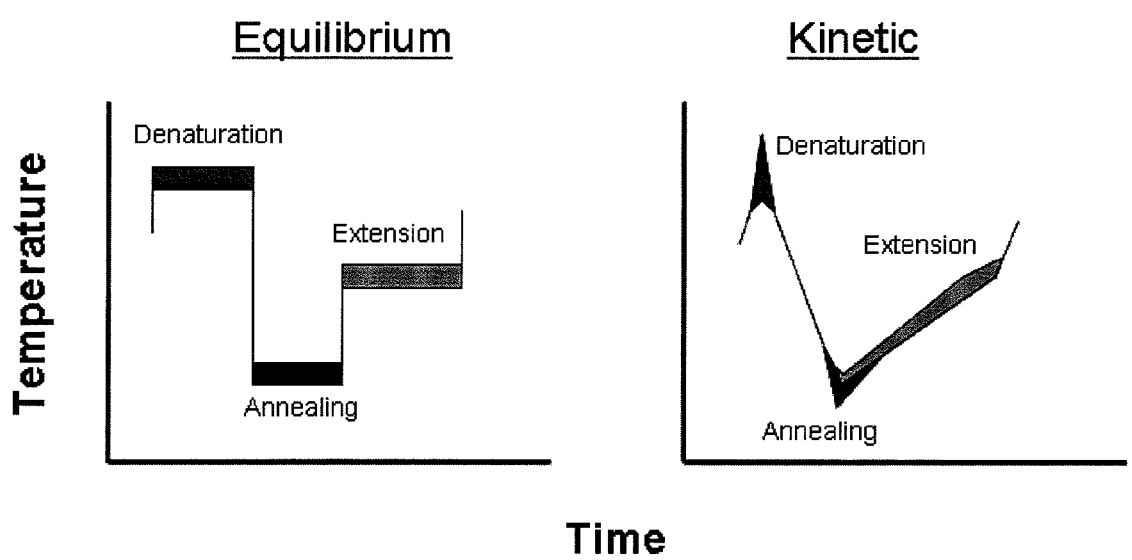
FIG. 15 shows two different versions of the PCR paradigm, both the "Equilibrium Paradigm", which shows the traditional model of PCR, in which a different temperature plateau exists for annealing, denaturing, and extension, and the "Kinetic Paradigm", which allows for faster amplification cycles, no loss in amplification efficiency, and superior amplification selectivity. Rapid cycling protocols founded upon the Kinetic Paradigm are currently used by the fastest of the commercially available PCR systems.

FIG. 15 compares the theoretical temperature cycling protocols associated with the two PCR paradigms. Rapid cycling protocols founded upon the Kinetic Paradigm are currently used by the fastest of the commercially available PCR systems.

Microchip PCR Platforms

Due to the PCR's wide expanse of biological applications and extensive use in so many research and clinical areas, much work is ongoing in both commercial and academic environments to improve the speed and precision of the process. A principal direction in which this research is moving is toward performing PCR in microfluidic chips. Doing so allows for a reduction in the thermal mass of the system and sample, lower reagent consumption, and possible integration with sample preparation processes, heating and cooling elements, and detection systems. The design and operation of microchip PCR can be divided into three principal categories: well-based PCR, shuttle PCR, and continuous-flow PCR. Well-based PCR is performed in a sample-containing chamber that is cyclically heated and cooled to the appropriate temperatures. This approach can produce PCR systems with the smallest footprint, but complex closed-loop control instrumentation is required to cycle the PCR sample through the required temperatures. Also, the thermal mass associated with the heater and PCR well limits the achievable thermal ramp rates of the solution. Shuttle PCR refers to techniques in which the thermal cycling is performed by shuttling small plugs of the PCR mixture back and forth between isolated temperature zones. The limitations set by the thermal mass of the system are eliminated by designing the temperature variations to occur spatially, instead of over time. The different thermal regions are established through local heating and/or cooling systems that maintain a specific section of the device at a unique steady state temperature. Although shuttle PCR removes the challenges associated with the time-dependent temperature cycling protocols of well-based systems, shuttle PCR introduces technical challenges with respect to the fluid handling, since the transport of the PCR mixture becomes the time-dependent feature of the device.

Continuous-flow PCR (CF-PCR) is performed by pumping the PCR mixture at a steady volume flow rate through a microfluidic channel that passes through different temperature regions. Similar to shuttle PCR, amplification can be performed with a steady-state temperature distribution. The sample transport for CF-PCR becomes trivial, since only a constant positive flow rate is required. The temperature cycling is achieved by fabricating a single serpentine channel that passes repeatedly through the distinct temperature regions of the microfluidic chip. Significant effort has been applied to improve the functionality and feasibility of the original design. Sun et al. have integrated transparent heating elements onto the microfluidic chip to improve the optical exposure of the channel. Obeid et al. have researched various port/interface arrangements on the chip, thus allowing for some cycle number selection. A number of research groups have included specific features that provide greater thermal isolation between the separate regions and/or to reduce the time the sample spends between the established PCR temperatures.

Thermal Gradient Platforms

Thermal gradients occur naturally as heat dissipates through material. With localized heating, regions in the vicinity of heating elements are hotter, while cooler temperatures exist further from the heat source. When net heat gains are eliminated, a steady state thermal gradient is established. The spatial variance in temperature (linear or higher-order) is a characteristic of the thermal conductivity of the material as well as the arrangement of the several heat sources and drains. Mao et al. have shown that linear thermal gradients can be generated for use with microfluidic chips. Thermal gradients of up to 25° C./mm were shown to be achievable. Cheng et al. used a radial temperature gradient to perform PCR. However, the device was designed such that the PCR sample was only to be shuttled between isothermal regions.

Methodology

A microfluidic channel running through a spatial temperature gradient was used to perform PCR, using a novel heating platform and a compatible microfluidic chip. The critical characteristics of the heater include the spatial rate of temperature change (° C./mm) and the overall range of temperatures. Features of the microfluidic chip must allow for an adequate number of thermal cycles, fast cooling rates, and moderate heating rates.

Heating Assembly

The heating of the microfluidic chips is achieved by placing single or multiple heaters (#HR5200, Minco, MN, USA) against the underside of the microchip. Both "centerline" and "edge" heating have been examined. Centerline heating involves placing a single heater down the middle of the chip. In this configuration, the middle of the chip is at the highest temperature (the denaturing temperature) while the temperature decreases to its coolest point at the outer edges of the chip. Heat dissipates to the atmosphere from all exposed surfaces of the chip. For the edge heating scheme, a single edge is held at a high temperature, while the opposite edge is in contact with a heat sink, through which the majority of the heat is drawn from the chip, thus creating the gradient from one side of the chip to the other. Both types of heating platforms were fabricated out of high temperature polymers (acrylic and/or Teflon), to which the heaters and the microchips were attached. FIG. 1 shows exploded CAD images of the assembled heater platforms.

Chip Design

During PCR cycling, as the sample cools from the denaturation temperature to the annealing temperature, single stranded product begins to form double stranded product, preventing further primer annealing. Therefore, this cooling should be as fast as possible. Since both annealing and denaturing occur nearly instantaneously, the PCR sample should not be held at these temperatures. The heating rate, specifically in the vicinity of the extension temperature, should be moderated according to the size of the product being amplified. Therefore, adapting a linear temperature gradient to an optimum PCR temperature cycle would require either: a) placing the microchannel at different angles in relation to the direction of the gradient, or b) flowing a sample at different velocities within each amplification cycle. This latter result can be achieved by changing the cross-sectional area of the channel within each cycle, as shown in FIG. 17. Li et al. have obtained substantial numerical and experimental data to show the effect of cross-sectional area on fluid velocity.

For reasons of compactness and ease of fabrication, the design of the thermal gradient PCR chip presented here incorporates variations in the channel widths to achieve optimum heating and cooling rates. For simplicity, these designs are such that the channels are wider in the regions where the fluid flow is from the annealing to the denaturing temperatures. Thus, the average heating ramp rate is established by the volume flow rate at the inlet to the device, while the ratio of the heating and cooling rates is determined by the geometry of the channel. In this manner, a constant volume fluid flow rate will produce optimum heating rates combined with rapid cooling.

FIG. 2 shows the general designs for both the centerline heating device and the edge heating assembly. For centerline heating, each PCR cycle begins in the narrow channel segment at the center of the chip. The sample rapidly cools as it moves toward the outer edge of the chip. The channel's farthest distance from the center of the chip corresponds to the annealing temperature of the PCR sample. As the channel turns and widens, the sample begins its moderate ramp through the extension temperature and to the denaturing temperature, where the one cycle ends and a successive cycle begins. The PCR chip for edge heating operates the same, only with the denaturing and annealing temperatures being on opposite edges of the chip, as explained previously.

Rapid Prototyping

Functional prototypes of the centerline heating chips have been fabricated using the recently developed "Xurographic" process. The "mask" for the fabrication consists of a two-dimensional outline of the channel geometry, drawn to scale in Adobe Illustrator CS (Adobe Systems, Inc., CA, USA). The design is then exported to a cutting plotter (Model #FC5100-75, Graphtec, CA, USA) where a very fine blade traces out the pattern on a double-coated adhesive tape (#9019, 3M, St. Paul, Minn.) which has a uniform thickness of 25 µm (30 µm, including adhesive). Tweezers are then used to "weed" the thin film by removing the interior of the cut channel design. The patterned film is then manually aligned and sandwiched between two pre-cleaned glass microscope slides (#12-550A, Fisher Scientific, NH, USA) that have been prepared with pre-drilled holes and Nanoport fluidic interconnects (Upchurch Scientific, WA, USA). The final step involves applying moderate pressure and curing at 65° C. for 20 minutes. Using this rapid prototyping method, a single thermal gradient chip can be fabricated in less than one hour. These chips were designed to include 22 amplification cycles. The channel widths were designed to be 1 mm and 200 µm for the heating and cooling sections, respectively, thus resulting in a 5:1 ratio between the average heating and cooling rates. Including segments for a longer initial denature and final extension, the overall channel length is approximately 25 cm, with a total volume on the order of 6 µl. The mask geometry is shown to scale in FIG. 2A. The lone circles in the mask design show the location of through-holes used to fasten the chip to the centerline heating platform.

Cleanroom Fabrication

Thermal gradient PCR chips for the edge heating PCR device were fabricated using mature microfabrication technologies. Initially, soda lime glass microscope slides (#12-550A, Fisher Scientific, NH, USA) were pre-cleaned with a piranha etch (3 H2SO4:1 H2O2) for ten minutes. A 900 nm thick film of chromium was then sputtered onto the glass blanks. Following the chromium deposition, a 2 µm thick layer of photoresist (Shipley, #1813) was spun onto the slides. The photoresist was exposed to UV light through a darkfield photomask, then developed and baked for 1 hour. The geometry of the exposed regions of the photomask is shown in FIG. 2B. After curing the photoresist, the glass was immersed into a chromium etchant to remove the exposed metal. With the cured photoresist and the thin chromium film serving as an etch mask for the top side of the glass, the backside of the glass was protected from the glass etchant with DuPont Kapton tape. The glass slides were then immersed in an etchant bath (1 HF:3 HNO3:10 H2O) for 34 minutes.

After stripping off the remaining photoresist and chromium, inlet and outlet holes were drilled through the patterned glass using a diamond-tipped drill bit and drill press. The glass slides were again cleaned in a piranha etch, along with an equal number of blank slides. Each patterned and drilled slide was then fused to a blank slide by baking at 620° C. for four hours. Upon cooling, a Nanoport fluidic interconnect (Upchurch Scientific, WA, USA) was attached over the inlet hole of each chip. The chip was designed to have 30 amplification cycles placed within the center 1 cm of the chip, as well as a longer initial denaturing time and final extension. The serpentine channel was to be 50 µm deep, and having widths of 650 µm and 110 µm for the heating and cooling regions, respectively. Considering the isotropic nature of the acid etch, these widths would correspond to a heating to cooling ratio of approximately 7:1.

Thermometry

To quantify the temperature profile generated across the PCR chips, it was necessary to measure the temperature extremes in addition to the general gradient shape. Thermocouples (#5SC-GG-K-30-3, Omega Engineering, CT, USA) were affixed over the locations corresponding to the annealing and denaturing regions of the microchannel. In addition, the entire surface of the chip was imaged with an infrared camera (Thermacam PM390, Inframetrics Inc., MA, USA).

Since borosilicate glass is partially transparent in the infrared spectrum, a number of sacrificial chips were coated with a flat black Krylon spray paint prior to assembly, thus giving these a known emissivity. Upon assembly of the device, current was applied to the heater(s) using a DC power supply (#E3642A, Agilent Technologies Inc., CA, USA). When the temperature equilibrated, the chips were characterized using both the thermocouple measurements and the IR data. Upon measuring the surface temperatures, it was assumed that the temperature of the glass at the depth of the channel was within 2° of surface temperature. Additionally, it was assumed that any PCR sample flowing through the channel would be within this same margin, as long as the fluid velocity was under 10 mm/s. These two assumptions were derived from experimental results previously published by other researchers.

Experimental

To determine the temperature gradient generated by the heater, infrared (IR) images were taken of the device while in operation.

Figure 16:
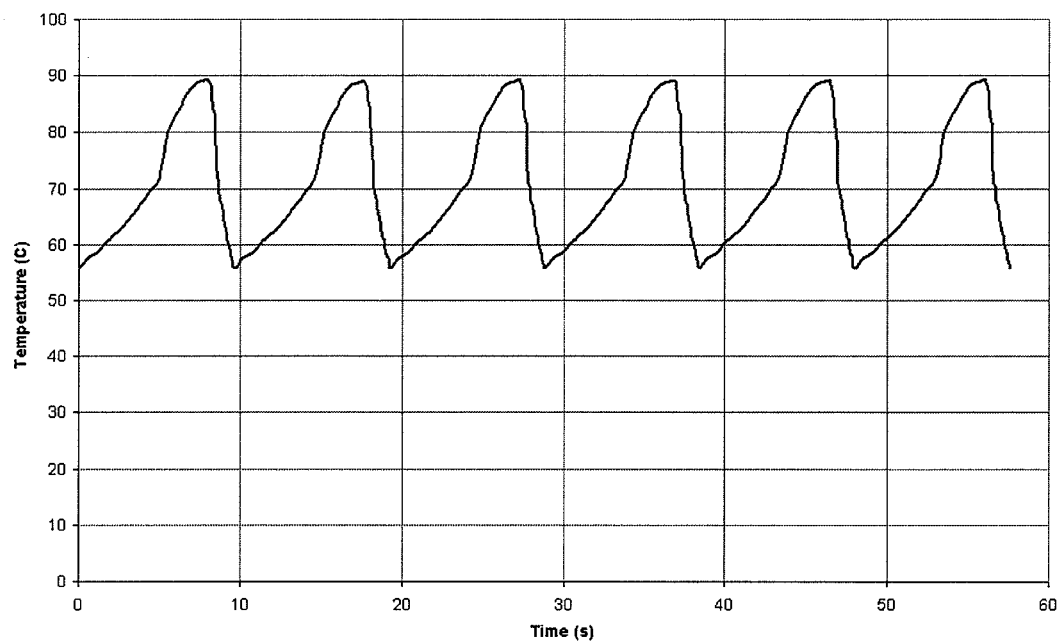
FIG. 16 shows a representative ramping profile using the thermal data. The widths of the channels for that particular device are 200µm/1000µm. A reasonable volume flow rate for amplification of smaller templates is 1.5µl/min.

After allowing the chip to heat up to an equilibrium state, PCR mixture is pumped into the chip at a constant volume flow rate. This is done by attaching an automated syringe pump to the fluidic interconnects on the chip. Local fluid velocities can be obtained from the known channel geometry and the known volume flow rate. An approximation of the thermal ramping can be made by combining spatial temperature information obtained from the IR data with the calculated velocities. FIG. 16 gives an example of such a profile.

To show that these devices are capable of amplifying DNA, a 75-bp segment of the Cystic Fibrosis gene exon 11 was amplified on both the thermal gradient PCR chip and an ultra-fast commercial thermocycler (LightCycler®, Roche, Indianapolis, Ind.). A 22-cycle amplification on the thermal gradient chip was performed in approximately 400 seconds, less than half the time required by the LightCycler®. The amplicon obtained from the thermal gradient chip was of a high purity and concentration, as can be seen by comparison against an identical sample amplified on the commercial equipment. The six samples compared with the single sample from the LightCycler® were all performed consecutively on the same device, the first being the one adjacent to the control sample.

CONCLUSION

Thermal gradient PCR can be used to amplify DNA targets. The specific benefits associated with the miniaturization of the PCR to the micro-scale can be found in many other works, and will not be summarized here. Specific to this research is the combination of the steady state spatial temperature gradient with a variable-velocity serpentine channel. This system is less complex to build and operate than other microfluidic PCR systems in the following ways: the temperature profile of the thermal gradient system is steady state, whereas well-based PCR systems have time-dependant thermal protocols. Eliminating this time domain allows for reduced instrumentation and makes thermal mass concerns virtually irrelevant. The sample flow is also steady state, thus eliminating the need for extensive fluid control systems common to the shuttle PCR approach. The thermal gradient, as a naturally occurring condition, is easily shaped and utilized, while shuttle and other continuous flow systems struggle against this phenomenon, seeking to reduce its effect by either incorporating additional insulating features or expanding the footprint of the device. Unhindered by such an obstacle, these thermal gradient devices have characteristically reduced channel length and footprint relative to other continuous flow systems. Where other continuous flow and shuttle systems incorporate multiple heating zones, each managed by an independent heater, sensor, and controller, the thermal gradient PCR device can operate with a single heater, having the entire required thermal spectrum forming around this one heat source. Such simplicity makes further advancements more attainable, such as those involving disposability, portability, and parallel processing.

It must be noted that as used herein and in the appended claims, the singular forms "a", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

REFERENCES

Belgrader, P.; Elkin, C. J.; Brown, S. B.; Nasarabadi, S. N.; Langlois, R. G.; Milanovich, F. P.; Colston Jr, B. W.; Marshall, G. D. *Analytical Chemistry,* 75: 3446-3450 (2003).

Cao, W.; Easley, C. J.; Ferrance, J. P.; Landers, J. P. *Analytical Chemistry,* 78:7222-7228 (2006).

Chiou, J. Matsudaira, P., Sonin, A. and Ehrlich, D. *Analytical Chemistry* 73:2018-2021 (2001).

Crews, N.; Gale, B.; Wittwer, C. *Biomedical Microdevices, in press* (2007).

Easley, C., Karlinsey, J. Bienvenue, J., Legendre, L., Roper, M., Feldman, S., Hughes, M., Hewlett, E., Merkel, T., Ferrance, J. and Landers, J. *PNAS* 103:19272-19277 (2006).

Fukuba, T., Yamamoto, T., Naganuma, T. and Fujii, T. *Chemical Engineering Journal* 101:151-156 (2004).

Garstecki, P.; Fuerstman, M. J.; Fischbach, M. A.; Sia, S. K.; Whitesides, G. M. *Lab on a Chip,* 6:207-212 (2006).

Handyside, A.; Kontogianni, E.; Hardy, K.; Winston, R. *Nature,* 344:768-770 (1990).

Hashimoto, M.; Chen, P. C.; Mitchell, M., Nikitopoulos, D.; Soper, S.; Murphy, M. *Lab on a Chip,* 4:638-645 (2004).

Herrmann, M.; Durtschi, J.; Bromley, L.; Wittwer, C.; Voelkerding, K. *Clinical Chemistry* 52:494-503 (2006).

Higuchi, R. *Bio/Technology* 11:1026 (1993).

Hill, C.; Duncan, A.; Wirth, D.; Nolte, F. *American Journal of Clinical Pathology,* 125:584-591 (2006).

Jendrejack, R., Dimalanta, E., Schwartz, D., Graham, M. and de Pablo, J. *Physical Review Letters* 91, (2003).

Kays, W. and Crawford, M. *Convective Heat and Mass Transfer,* McGraw-Hill, New York, (1993).

Kopp, M.; de Mello, A.; Manz, A. *Science,* 280:1046-1048 (1998).

Lapham, J., Rife, J., Moore, P. and Crothers, D. *Journal of Biomolecular Nmr* 10:255-262 (1997).

Li, S.; Fozdar, D.; Ali, M.; Li, H.; Shao, D.; Vykoukal, D.; Vykoukal, J.; Floriano, P.; Olsen, M.; McDevitt, J.; Gascoyne, P.; Chen, S. *Journal of Microelectromechanical Systems,* 15:223-236 (2006).

Mao, H.; Holden, M.; You, M.; Cremer, P. *Analytical Chemistry,* 74:5071-5075 (2002).

Montgomery, J. (2007).

Morrison, T.; Hurley, J.; Garcia, J.; Yoder, K.; Katz, A.; Roberts, D.; Cho, J.; Kanigan, T.; Ilyin, S. E.; Horowitz, D.; Dixon, J. M.; Brenan, C. J. H. *Nucl. Acids Res.,* 34: e123- (2006).

Nakayama, T.; Kurosawa, Y.; Furui, S.; Kerman, K.; Kobayashi, M.; Rao, S. R.; Yonezawa, Y.; Nakano, K.; Hino, A.; Yamamura, S.; Takamura, Y.; Tamiya, E. *Analytical and Bioanalytical Chemistry,* 386:1327-1333 (2006).

Neuzil, P.; Pipper, J.; Hsieh, T. Molecular *Biosystems,* 2:292-298 (2006).

Northrup, M.; Benett, B.; Hadley, D.; Landre, P.; Lehew, S.; Richards, J.; Stratton, P. *Anal. Chem.* 70:918-922 (1998).

Obeid, P. and Christopoulos, T. *Analytica Chimica Acta* 494: 1-9 (2003a).

Obeid, P., Christopoulos, T., Crabtree, H. and Backhouse, C. *Analytical Chemistry* 75:288-295 (2003b).

Pappaert, K., Biesemans, J., Clicq, D., Vankrunkelsven, S. and Desmet, G. *Lab on a Chip* 5:1104-1110 (2005).

Ririe, K.; Rasmussen, R.; Wittwer, C. *Analytical Biochemistry* 1997, 245:154-160.

Roper, M., Easley, D., Legendre, L., Humphrey, J. and Landers, J. *Analytical Chemistry* 79:1294-1300 (2007).

Schneegass, I.; Brautigam, R.; Kohler, J. M. *Lab on a Chip,* 1:42-49 (2001).

Simpson, P., Woolley, A. and Mathies, R. *Biomedical Microdevices* 1:7-25 (1998).

Sun, K., Yamaguchi, A., Ishida, Y., Matsuo, S. and Misawa, H. *Sensors and Actuators, B: Chemical* 84:283-289 (2002).

Sundberg, S.; Wittwer, C.; Greer, J.; Pryor, R.; Elenitoba-Johnson, O.; Gale, B. *Biomedical Microdevices,* 9:159-166 (2007).

Wang, H., Chen, J., Zhu, L., Shadpour, H., Hupert, M. and Soper, S. *Analytical Chemistry* 78:6223-6231 (2006).

Wittwer, C.; Reed, G.; Ririe, K. In *The Polymerase Chain Reaction;* Mullis, K. B., Ferre, F., Gibbs, R., Eds.; Springer-Verlag: Deerfield Beach, pp 174-181 (1994).

Wittwer, C.; Reed, G.; Gundry, C.; Vandersteen, J. G.; Pryor, R. *J. Clin Chem,* 49:853-860 (2003).

Wittwer, C.; Hermann, M. In *PCR Applications: Protocols for Functional Genomics,* 1 ed.; Innis, M. A., Gelfand, D. H., Sninsky, J. J., Eds.; Academic Press: San Diego, pp 211-229 (1999).

Yang, M., Pal, R. and Burns, M. *Journal of Micromechanics and Microengineering* 15:221-230 (2005).

Zhang, C.; Xu, J.; Ma, W.; Zheng, W. *Biotechnology Advances,* 24:243-284 (2006).

Zhang, C.; Xing, D. *Nucl. Acids Res.,* gkm389 (2007).

Zhou, L.; Wang, L.; Palais, R.; Pryor, R.; Wittwer, C. *Clinical Chemistry,* 51:1770-1777 (2005).

We claim:

1. A device for replicating nucleic acid, said device comprising: a microchannel extending from an inlet port to an outlet port; and a heater or heaters for producing a spatial temperature gradient, wherein the microchannel has a heating portion and a cooling portion, wherein each portion of the microchannel has a width, wherein the width of the heating portion is wider than the width of the cooling portion, and wherein the heater or heaters are located adjacent to the transition from the heating portion to the cooling portion.

2. The device of claim 1, wherein the microchannel forms a serpentine pattern over the temperature gradient.

3. The device of claim 1, wherein the temperature gradient allows for gradual heating of the sample.

4. The device of claim 1, wherein the temperature gradient is a steady-state gradient.

5. The device of claim 1, wherein the heater or heaters is disposed at the far edges of the device, away from the microchannel.

6. The device of claim 1, wherein the heater is disposed along a centerline of the microchannel.

7. The device of claim 1, wherein the device also comprises a cooling component.

8. The device of claim 7, wherein the cooling component cools by air.

9. The device of claim 7, wherein the cooling component cools by using cooling fins.

10. The device of claim 7, wherein the cooling component is a thermoelectric cooler.

11. The device of claim 1, wherein the spatial temperature gradient is between approximately 1° C. and 50° C. or more per millimeter.

12. The device of claim 7, further comprising a pump for pumping fluid through the microchannel.

13. The device of claim 1, further having a light source for emitting light to thereby cause fluorescence.

14. The device of claim 13, further comprising a sensor for measuring the spatial distribution of fluorescence.

15. The device of claim 1, wherein the microchannel is formed in a thin film sandwiched between two plates.

16. The device of claim 1, wherein the microchannel has a channel depth of between 10 and 200 μm.

17. The device of claim 11, wherein the cooling portion of the microchannel has a width of approximately 30-500 μm.

18. The device of claim 1, wherein the heating portion of the microchannel has a width of approximately 5-5000 μm.

19. The device of claim 1, wherein the microchannel performs between 20 and 50 amplification cycles.

20. The device of claim 1, wherein the microchannel has a length of approximately 1 to 100 centimeters.

21. The device of claim 1, wherein the microchannel is formed using a Xurography process.

22. The device of claim 1, wherein the microchannel is formed using a wet etching process.

23. The device of claim 1, wherein the heater or heaters is maintained at a steady temperature.

24. A device for replicating a nucleic acid, said device comprising: a microchannel; two plates; and a heater; wherein the microchannel is sandwiched between the two plates and the heater is operable to form a spatial temperature gradient across the microchannel, the microchannel has a heating portion and a cooling portion, wherein each portion of the microchannel has a width, wherein the width of the heating portion is wider than the width of the cooling portion, and wherein the heater or heaters are located adjacent to the transition from the heating portion to the cooling portion.

25. The device of claim 24, wherein the microchannel is comprised of a thin film.

26. The device of claim 25, wherein the microchannel is created using at least one of Xurography and glass etching.

27. The device of claim 25, wherein the microchannel has a serpentine pattern.

28. The device of claim 25, further comprising at least one fastener for holding the two plates together.

29. A device for replicating nucleic acid, said device comprising: a channel having a plurality of sections forming a continuous pattern; and a heater disposed along a centerline of the continuous pattern; wherein each section of the channel comprises a first portion and a second portion, the first portion of the channel being narrower than the second portion of the channel, wherein the first portion of the channel is a heating portion and the second portion of the channel is a cooling portion, and wherein the heater or heaters are located adjacent to the transition from the heating portion to the cooling portion.

30. The device of claim 29, wherein the wide and narrow portions are determined by the heating and cooling sections of the device.

31. The device of claim 30, wherein the dimensions of the device determine the velocity of the fluid therein, thereby controlling the temperature ramp rates.

32. The device of claim 31, wherein the continuous pattern is a serpentine pattern.

33. The device of claim 31, further comprising a pump for pumping fluid through the channel.

34. A method of amplifying a nucleic acid, the method comprising the steps of:
a) forming a steady state temperature gradient on a device comprising microchannels and a heater or heaters, wherein the microchannel has a heating portion and a cooling portion, wherein each portion of the microchannel has a width, wherein the width of the heating portion is wider than the width of the cooling portion, and wherein the heater or heaters are located adjacent to the transition from the heating portion to the cooling portion; and
b) exposing a nucleic acid to the temperature gradient in a manner conducive for amplification; thereby amplifying a nucleic acid.

35. The method of claim 34, wherein the microchannel is in a serpentine pattern.

36. The method of claim 34, wherein the nucleic acid is amplified multiple times.

37. The method of claim 34, further comprising detecting nucleic acid amplification using fluorescent monitoring; thereby monitoring nucleic acid amplification using a microchip.

38. The method of claim 37, wherein the nucleic acid is detected by exposing the nucleic acid to a dye, then detecting interaction of the dye and the nucleic acid.

39. The method of claim 38, wherein the dye is fluorescent.

40. The method of claim 38, wherein the dye is intercalating.

41. The method of claim 37, wherein each cycle of nucleic acid replication can be detected.

42. The method of claim 37, wherein amplification can be detected with a single photograph.

43. The method of claim 41 further comprising the step of measuring the amount of fluorescence produced by the dye after each extension.

44. The method of claim 43, wherein amplification is detected by monitoring the channel-wise growth in fluorescence and wherein the melting behavior of the amplicon is detected during each denaturing process.

45. The method of claim 44, further comprising the step of providing the information in real time.

46. The method of claim 37 wherein the nucleic acid is pumped into the microchannel.

47. The method of claim 46 wherein the nucleic acid is pumped into the microchannel using continuous flow.

48. The method of claim 37, wherein detecting nucleic acid further comprises determining information related to the denaturing or melting of the double stranded nucleic acid.

49. The method of claim 38, wherein the dye is at least one of SYBR Green, LC Green, and LC Green Plus.

50. The method of claim 44, wherein a melting curve analysis is conducted on the nucleic acid.

51. The method of claim 37, wherein more than one nucleic acid sample is amplified at a time.

52. The method of claim 51, wherein the nucleic acid samples differ in sequence.

53. The method of claim 52, wherein an analysis of the spatial fluorescence and temperature distribution can distinguish between the multiple samples of nucleic acids.

* * * * *

UNITED STATES PATENT AND TRADEMARK OFFICE
CERTIFICATE OF CORRECTION

| | | |
|---|---|---|
| PATENT NO. | : 8,263,392 B2 | Page 1 of 1 |
| APPLICATION NO. | : 12/514671 | |
| DATED | : September 11, 2012 | |
| INVENTOR(S) | : Bruce Kent Gale, Niel Davenport Crews and Carl Thomas Wittwer | |

It is certified that error appears in the above-identified patent and that said Letters Patent is hereby corrected as shown below:

In the Specification

In Column 3, lines 9-15, delete "Fig. 1 shows an exploded diagram of the heating apparatus designed for use with thermal gradient PCR. FIG. 1A shows a centerline heating assembly, while FIG. 1B shows an edge heating assembly. Aluminum pieces thermally interface the glass chip with the heaters and cooling fins, ensuring a uniform termperature gradient across the glass. The Teflon pieces hold the heating elements in place.".

In Column 3, immediately following line 26, please insert --FIG. 2 shows an exploded diagram of the heating apparatus designed for use with thermal gradient PCR. FIG. 2A shows a centerline heating assembly, while FIG. 2B shows an edge heating assembly. Aluminum pieces thermally interface the glass chip with the heaters and cooling fins, ensuring a uniform temperature gradient across the glass. The Teflon pieces hold the heating elements in place.--.

In Column 3, line 27, replace "FIG. 2" with --FIG. 3--.

In Column 3, line 41, replace "FIG. 3" with --FIG. 4--.

In Column 3, line 46, replace "FIG. 4" with --FIG. 5--.

Figure 6:
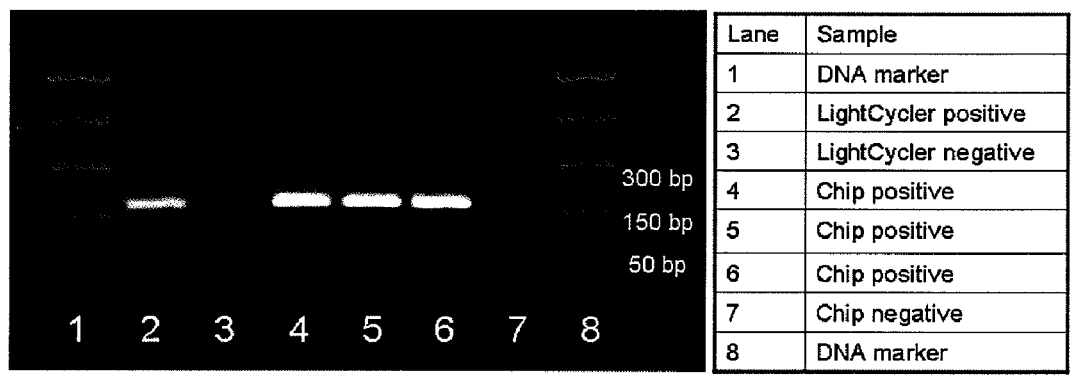

In Column 3, line 52, replace "FIG. 5" with --FIG. 6--.

Signed and Sealed this
Twenty-fifth Day of August, 2015

Michelle K. Lee
*Director of the United States Patent and Trademark Office*

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 1
ggttcgtcaa ggactggttt                                             20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 2
ttgaacagca tcggactcag                                             20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 3
gcttccatga cgcagaagtt                                             20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 4
gcgaaaggtc gcaaagtaag                                             20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 5
attacactac attcccttcc a                                           21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: NOte = Synthetic Construct

<400> SEQUENCE: 6

-continued

```
agtgaaattg tatgcagtag a                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 7
gaattttggg atggggaaga g                                              21

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 8
tccagtaagg tcagtgatat gg                                             22

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 9
catgcaagac aggagcca                                                  18

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 10
tgggaatgag atagtttctg aattta                                         26
```